United States Patent [19]

Ens et al.

[11] Patent Number: 4,618,230

[45] Date of Patent: Oct. 21, 1986

[54] VISUAL STIMULATOR

[75] Inventors: John Ens, Burnaby; James A. McEwen, Richmond; Craig W. Beattie, Burnaby, all of Canada

[73] Assignee: Vancouver General Hospital, Vancouver, Canada

[21] Appl. No.: 391,972

[22] Filed: Jun. 24, 1982

[51] Int. Cl.$^4$ .............................................. A61B 3/10
[52] U.S. Cl. .................................... 351/221; 351/211
[58] Field of Search ................ 356/404; 351/206, 211, 351/221

[56] References Cited

U.S. PATENT DOCUMENTS

| | | |
|---|---|---|
| 2,166,947 | 7/1939 | Fayerweather . |
| 3,242,344 | 3/1966 | Zuckerbraun . |
| 3,303,271 | 2/1967 | Hecker . |
| 3,409,905 | 11/1968 | Bemrose et al. . |
| 3,514,191 | 5/1970 | Hoskin . |
| 3,518,930 | 7/1970 | Thieme et al. . |
| 3,561,847 | 2/1971 | Kitsopoulos et al. . |
| 3,632,192 | 1/1972 | Grib . |
| 3,639,041 | 2/1972 | Cornsweet .......................... 351/211 |
| 3,879,113 | 4/1975 | Howland et al. . |
| 4,033,693 | 7/1977 | Payrhammer et al. . |
| 4,060,313 | 11/1977 | Kondo . |
| 4,109,237 | 8/1978 | Hill . |
| 4,135,791 | 1/1979 | Govignon . |
| 4,208,107 | 6/1980 | Oharek . |
| 4,238,142 | 12/1980 | Richards et al. . |
| 4,251,139 | 2/1981 | Matsumura . |
| 4,257,687 | 3/1981 | Kohayakawa . |
| 4,265,518 | 5/1981 | Matsumura . |
| 4,266,862 | 5/1981 | Trotscher et al. ................... 351/211 |
| 4,312,574 | 1/1982 | Wilms . |
| 4,370,033 | 1/1983 | Kani et al. ........................... 351/211 |

OTHER PUBLICATIONS

Intensity of Stimulation and Rod and Cone Response in Clinical Electroretinography; Brunette et al; Canadian Journal of Ophthalmology 13:27, 1978.
ERG Responses of Rods and Cones During Dark Adaptation; Brunette et al; Canadian Journal of Ophthalmology 13:186, 1978.
VGH Develops Improved Testing Stimulator; Life Line Magazine, vol. 1, No. 3, Sep., 1979, pp. 14-15.
An Improved ERG Stimulator which Uses Microprocessor Control; Cavazzi et al; Digest of the Eighth Canadian Medical and Biological Engineering Conference; Aug., 1980.
An Improved ERG Stimulator; Ens, Text of Oral Presentation at the Eighth Canadian Medical and Biological Engineering Conference; Aug., 1980.
Evoked Response System; product brochure No. S832H78-Aug., 1978; Grass Medical Instruments; Quincy, Mass.
Visual Electrophysiology Test Instruments; product brochure of Life-Tech Instruments, Inc.; Houston, Tex.
Electroretinograph Electro-Oculograph Instrumentation; product brochure of LKC Systems, Inc.; Gaithersburg, Md.
Electrodiagnostic Instrumentation for Routine and Clinical Research Recordings; product brochure of LKC Systems, Inc.; Gaithersburg, Md.
Ophthalmic Electrophysiologic Testing Systems; product brochure of LKC Systems, Inc.; Gaithersburg, Md.
ERG EOG VEP Testing Made Practical; product brochure of Nicolet Biomedical Instruments; Madison, Wis.

Primary Examiner—Rodney B. Bovernick
Attorney, Agent, or Firm—Klarquist, Sparkman, Campbell, Leigh & Whinston

[57] ABSTRACT

A visual stimulator for light stimulation of a subject's eyes to obtain electroretinogram, electro-oculogram or visually evoked potential responses. The stimulator comprises a light directing means for directing light from a light source into the subject's eyes, attenuator means for selectably attenuating the light source, photodetector means for producing an output signal representative of the radiant energy directed into the subject's eyes and signal processing means for receiving and processing the output signal to derive therefrom further output signals representative of the radiometric or photometric characteristics of said radiant energy. A light shutter comprising first and second shutter leaves affixed to the shafts of first and second galvanometers is also provided. The shutter leaves are positioned for pivotal movement with the galvanometer shafts to attenuate light passing between the shutter leaves. Attenuation control means is provided for selectably varying current signals applied to the galvanometers to selectably pivot the shutter leaves, thereby selectably varying the attenuation of light passing between the shutter leaves.

8 Claims, 11 Drawing Figures

VISUAL STIMULATOR

FIELD OF THE INVENTION

This application pertains to visual stimulators for stimulating the visual system to assist in recording its electrophysiological responses. More particularly, the application pertains to visual stimulator apparatus for stimulating the visual system to obtain an electroretinogram, a visual evoked potential or an electro-oculogram. In the art, the term "ERG/VEP/EOG stimulator" is often used to describe such apparatus.

BACKGROUND OF THE INVENTION

When light strikes the retina of the eye, the photoreceptors in the retina (rods and cones) respond by generating a small electrical potential. The aggregate electrical potential representing the total response of all the rods and cones in the retina to a brief flash of light is an electroretinogram (hereinafter "ERG"). An ERG, together with other measurements, may be used by ophthalmologists to help determine the functional status of the retina in various conditions including congenital and acquired degenerative state, trauma (injuries), toxic states and inflammatory diseases.

An ERG may be obtained by photostimulating the retina. Conventionally, a light flash of several milliseconds duration is directed into the subject's eyes. The flash intensity must be variable so that the subject's ERG response can be evaluated throughout a broad range of adaptational states. In low ambient light conditions (dark adaptation), it is mainly rod photoreceptors which mediate visual sensation while in high ambient light conditions (light adaptation) cones dominate visual processes. Rod function is best evaluated with low intensity light flashes while cones respond to flashes of much greater intensity. Rod and cone function may also be differentiated by varying the chromatic properties of the light flash. Short wavelength (blue) stimuli are more effective in generating rod responses while long wavelength (red) stimuli produce mainly cone responses. Thus it is preferable to make provision for both variable flash intensity and chromatic filtering of the light stimulus.

The subject's ERG response is measured with a special corneal contact electrode. Usually, the response is displayed and stored for later analysis.

A typical prior art ERG stimulator comprises a reflective hemispherical bowl and a controllable light source for illuminating the bowl. The subject is fitted with the corneal contact electrode and then looks into the bowl as it is illuminated. Conventionally, three separate tests are used to measure the subject's ERG response. The first test is carried out in dark adaptation, following a specific period of time in dark ambient conditions sufficient to allow rod photoreceptor function to be fully expressed and well below the threshold at which cone function may occur. The eyes are then stimulated with a single light flash. The procedure is repeated, increasing the flash intensity in approximately three decibel (hereinafter "dB") steps over a maximum range of about 36 dB until an ERG with a peak of at least 50 microvolts (hereinafter "uV") is recorded. The 50 uV threshold is an arbitrary criterion threshold for photoreceptor response amplitudes broadly accepted within the clinical community. Following determination of the 50 uV threshold, responses are obtained at higher stimulus intensities, sufficient to evoke mixed rod and cone responses in order to evaluate more complex interactions between both classes of photoreceptors. The second test is carried out in light adaptation, following a brief period of time in ambient light of sufficient intensity to suppress rod function. A 50 uV threshold is determined for cone responses, followed by stimulation at higher intensities to elicit other components of the ERG having clinical significance in light adaptation. The third test is also carried out in light adaptation, a high intensity light source being presented at a stimulus frequency of about 30 Hertz (in contrast to the first and second tests in which the stimulus frequency is generally about 1 Hertz.) This higher frequency stimulus tests the temporal response characteristics of the cone photoreceptors, thus yielding further information regarding functional characteristics of these retinal cells.

The ERG represents the transient electrical responses of the retina to brief flashes of light, superimposed upon a more or less constant electrical potential originating in retinal structures, and present in both dark and light adaptation. The record of this "constant" or "standing" electrical potential is called the electro-oculogram (hereinafter "EOG"). Typically, the amplitude of this potential is considerably less in dark adaptation than in light adaptation. The ratio of the maximum amplitude in light adaptation to the minimum amplitude in dark adaptation is of clinical significance and is a useful adjunct to interpretation of the ERG in some disorders, as well as having importance in its own right in certain hereditary retinal degenerative conditions.

The "standing" potential referred to above is obtained by means of electrodes located horizontally adjacent to the eyes on the skin surface. Measurement of this potential is facilitated by instructing the subject to alternate his or her direction of gaze between two clearly indicated fixation targets placed 15° horizontally eccentric to a reference point directly in front of the subject. Typically, the fixation targets are placed within the same hemispherical bowl used in the ERG test. Thus conditions exist such that the same apparatus used to present the appropriate background ambient light for the ERG can also be employed to present an appropriate background light ambience for the EOG test. An EOG test is commonly performed in three stages: a brief initial phase in which the subject views the fixation targets in light adaptive conditions, followed by a second phase in dark adaptation during which the subject views the dimly illuminated fixation targets and concluding with a third phase in light adaptation (the second and third phases each being of about 15 minutes duration).

The amplified electrical responses obtained during the three phases of the EOG procedure are commonly recorded on a slowly moving strip of chart paper over the duration of the test. At the conclusion of the test, the recording is analysed in order to determine those times at which the minimum and maximum responses in dark and light have occurred, followed by calculation of the ratio of those responses.

Photostimulation of the eye causes the generation of electrical potentials from the visual system in addition to the ERG and EOG. One other such potential, recorded from electrodes attached to the scalp of a test subject, is called the visually evoked potential (hereinafter "VEP") or visually evoked cortical potential ("VECP"). The VEP is a very small electrical signal and must be differentiated from other electrical activity occurring on the surface of the scalp by computer assisted signal processing procedures. An extremely wide variety of visual stimuli can be employed to elicit a VEP, one of the most commonly employed being a diffuse flash of light presented at some chosen temporal frequency within the field of vision. Stimulus frequencies generally range between 0.5 and 60 Hertz. The VEP largely reflects functional properties of the central cone-rich portion of the retina as well as conduction characteristics within the visual pathways leading to the visual cortex of the brain. The principal clinical application of the VEP relates to the evaluation of inflammatory and degenerative abnormalities of the optic nerves and posterior visual pathways.

Many problems have been encountered with prior art visual stimulators. The greatest difficulties have related to the source, regulation, measurement and calibration of the light flash stimulus. Most prior art visual stimulators have incorporated a stroboscopic gas discharge tube. Such sources have phipiologically undesirable spectral characteristics and stimulus energy is difficult to regulate. Measurements of the photometric and radiometric characteristics of the flash radiant energy are also difficult to obtain with such sources and in most cases flash energy declines to some extent as stimulus frequency increases. Prior art visual stimulator apparatus is often cumbersome and inflexible, making it difficult to test subjects in both upright and supine positions. Various difficulties have been encountered with respect to obtaining a permanent record of the responses obtained during ERG, EOG and VEP testing. The EOG in particular has been cumbersome to deal with due to the length of the continuously recorded potential.

The present invention addresses the foregoing disadvantages. For example, the light source of the preferred embodiment is an incandescent filament with a continuous spectrum having physiologically desirable chromatic characteristics. Energy emitted from this source is very stable. Of particular importance is the means used to interrupt the transmission of the light stimulus from the source to the subject's eyes and to regulate stimulus duration together with stimulus intensity. Means are provided which permit fine incremental control of stimulus intensity (attenuation) over a broad range of energy levels. Measurement of stimulus energy and luminance is provided and allows display of stimulus parameters in absolute radiometric and photometric units. The photodetector device employed in the preferred embodiment to obtain these measurements also mediates the self-calibration system incorporated in the preferred embodiment, ensuring a very high degree of control over the light stimulus reaching the subject's eyes. Provision is made for altering the chromatic characteristics of the stimulus in accordance with testing requirements. Another feature incorporated in the preferred embodiment is a means by which the response obtained from the ERG, EOG or VEP procedure can be transferred to a hard-copy record together with a reproduction of stimulus parameters on the same hard-copy record. This is of special significance with respect to the EOG response in that the results of a long recording procedure can be condensed into a compact hard-copy record.

The features described briefly above have been embodied in a device of sufficiently small size and flexibility to allow testing of subjects in a wide range of anatomical positions, and sufficiently mobile to allow testing in many clinical environments.

SUMMARY OF THE INVENTION

The invention is directed, in one aspect, to a visual stimulator comprising light directing means for directing light from a light source into a subject's eye; attenuator means for selectably attenuating the light source; photodetector means for producing a first output signal representative of the radiant energy directed into the subject's eye; and, signal processing means for receiving and processing the first output signal to derive therefrom further output signals representative of the photometric or radiometric characteristics of said radiant energy. Display means is provided for displaying the radiometric or photometric characteristics so derived.

Preferably, the attenuator means comprises a light shutter which is another aspect of the invention. The light shutter comprises a first shutter leaf affixed to a first galvanometer shaft, and a second shutter leaf affixed to a second galvanometer shaft; the shutter leaves being positioned for pivotal movement with the galvanometer shafts to attenuate light passing between the shutter leaves. Control means are provided to enable repeated application of selectably variable current signals to the galvanometers, thereby interrupting and selectably attenuating the light source.

The first shutter leaf has a first notch and the second shutter leaf has a second notch. The shutter leaves are positioned to define a light attenuating aperture between the notches. The shutter leaves and notches are further positioned such that pivotal movment of the shutter leaves varies the area of the aperture, thereby varying the attenuation of light by the shutter. Advantageously, the notches are shaped such that the aperture area varies in proportion to the exponential of the distance between the shutter leaves.

Advantageously, the aforementioned "further output signals" include a second output signal representative of the light flux at the photodetector means. The signal processing means compares the second output signal with a calibration signal representative of the light flux expected from the light source and produces an out-of-calibration alarm signal if the signals differ by more than a pre-selected amount.

Other features of the invention are defined in the appended claims.

DESCRIPTION OF THE PREFERRED EMBODIMENT

I. Introduction

Figure 1:
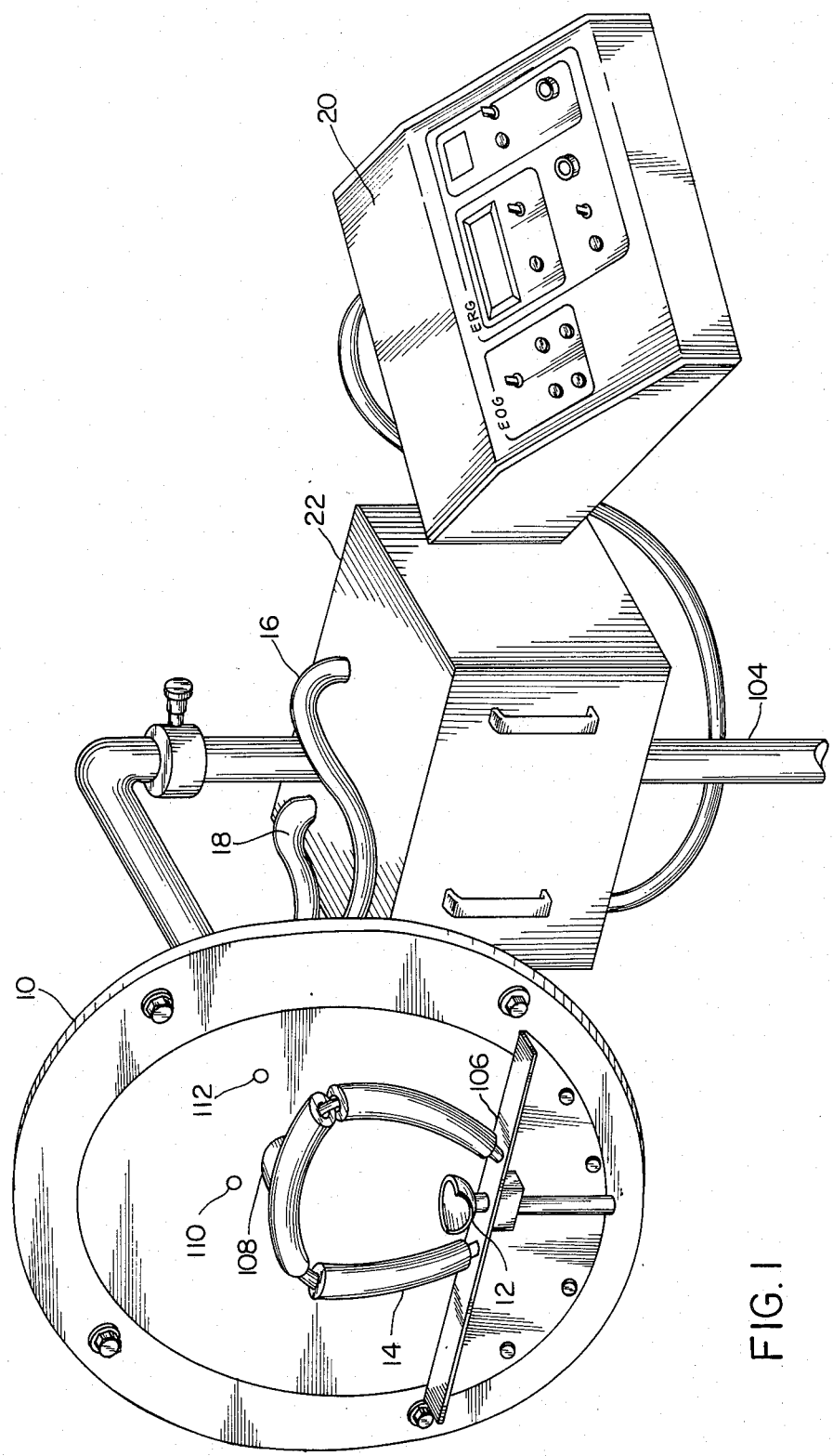
FIG. 1 is a pictorial representation of a visual stimulator according to the preferred embodiment.

FIG. 1 is a pictorial representation of a visual stimulator according to the preferred embodiment. A reflectively coated hemispherical stimulator bowl 10 is placed in front of the subject. The subject is fitted with a corneal contact electrode and is then positioned to look into the stimulator bowl by resting his chin on chin rest 12 and by resting his head against head rest 14. Fibre optics cables 16 and 18 convey light for illuminating bowl 10 from, respectively, a background light source and a flashlight source (hereinafter described in greater detail). Stimulator bowl 10 serves as a "light directing means" for directing light from the light sources into the subject's eyes. As an alternative light directing means, the subject could be fitted with a pair of goggles coupled to the fibre optics cables.

A control console 20 is provided to enable the selection of various operating parameters. For example, the operator may, with the aid of control console 20, control the timing, intensity, duration and chromatic filtration of light flashed in stimulator bowl 10, all as hereinafter explained. Control console 20 includes a display for providing the operator with a visual indication of the background irradiance within bowl 10 and of the radiant energy of each light flash which illuminates bowl 10.

Optics box 22 contains a background light section for providing a controlled background irradiance which is conveyed to stimulator bowl 10 by fibre optics cable 16. Optics box 22 also contains a flashlight section for producing controlled flashes of light which are conveyed to stimulator bowl 10 by fibre optics cable 18. The background light section provides controlled ambient light conditions to produce the light adaptational states required to elicit rod and/or cone response, as required. The flashlight section provides the stimulating light flashes necessary for ERG and VEP testing.

II. Background Light Section

Figure 8:
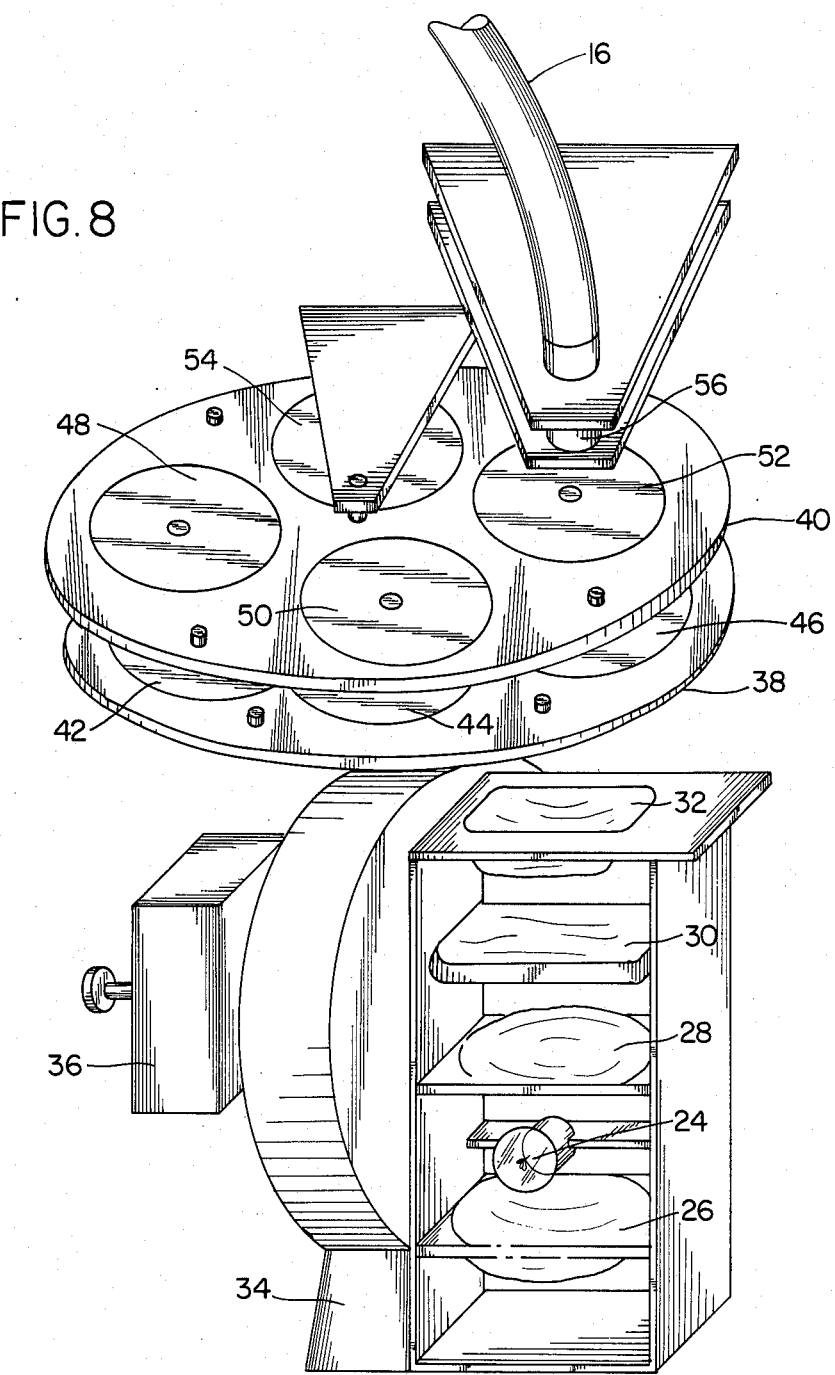
FIG. 8 is a pictorial representation of the optics portion of the background light section of the preferred embodiment.

FIG. 8 is a pictorial representation of the optics portion of the background light section of the preferred embodiment. The background light section includes a vertically mounted light source and associated condensing optics obtained from a Rollei P350A slide projector. The light source and condensing optics includes a lightbulb 24 and associated reflector 26, converging lens 28, infra-red filter 30 and a further converging lens 32. The Rollei P350A cooling fan 34 and its drive motor 36 are also used. Lightbulb 24 is a Philips FCS 24-volt, 150-watt lightbulb.

Two aluminium disks 38 and 40 are rotatably mounted above the light source. Disk 38 is fitted with three chromatic filters 42, 44 and 46 (red, blue and green) which are positioned in disk 38 for alignment over the light source as disk 38 is manually rotated. Disk 38 also contains a hole having no filter which may be positioned over the light source if "white" (i.e. no) chromatic filtration is desired. Disk 40 is of the same size and shape as disk 38 and is rotatably mounted immediately above disk 38. Disk 40 contains four apertures 48, 50, 52 and 54 of preselected diameters which are positioned in disk 40 for alignment over the light source as disk 40 is manually rotated. The edges of disks 38 and 40 protrude slightly from the side of optics box 22, as shown in FIG. 1, so that the operator may manually rotate the disks. Magnetic stops are provided on disks 38 and 40 so that the operator may "feel" when the disks have been properly positioned with a filter or aperture in alignment over the light source.

A final converging lens 56 is mounted above disks 38 and 40 at the base of fibre optics cable 16. When lightbulb 24 is illuminated, light therefrom is focused on the end of fibre optics cable 16, after filtration by whichever of the filters in disk 38 has been selected and after attenuation by whichever of the apertures in disk 40 has been selected.

III. Flashlight Section and Light Shutter

Figure 7:
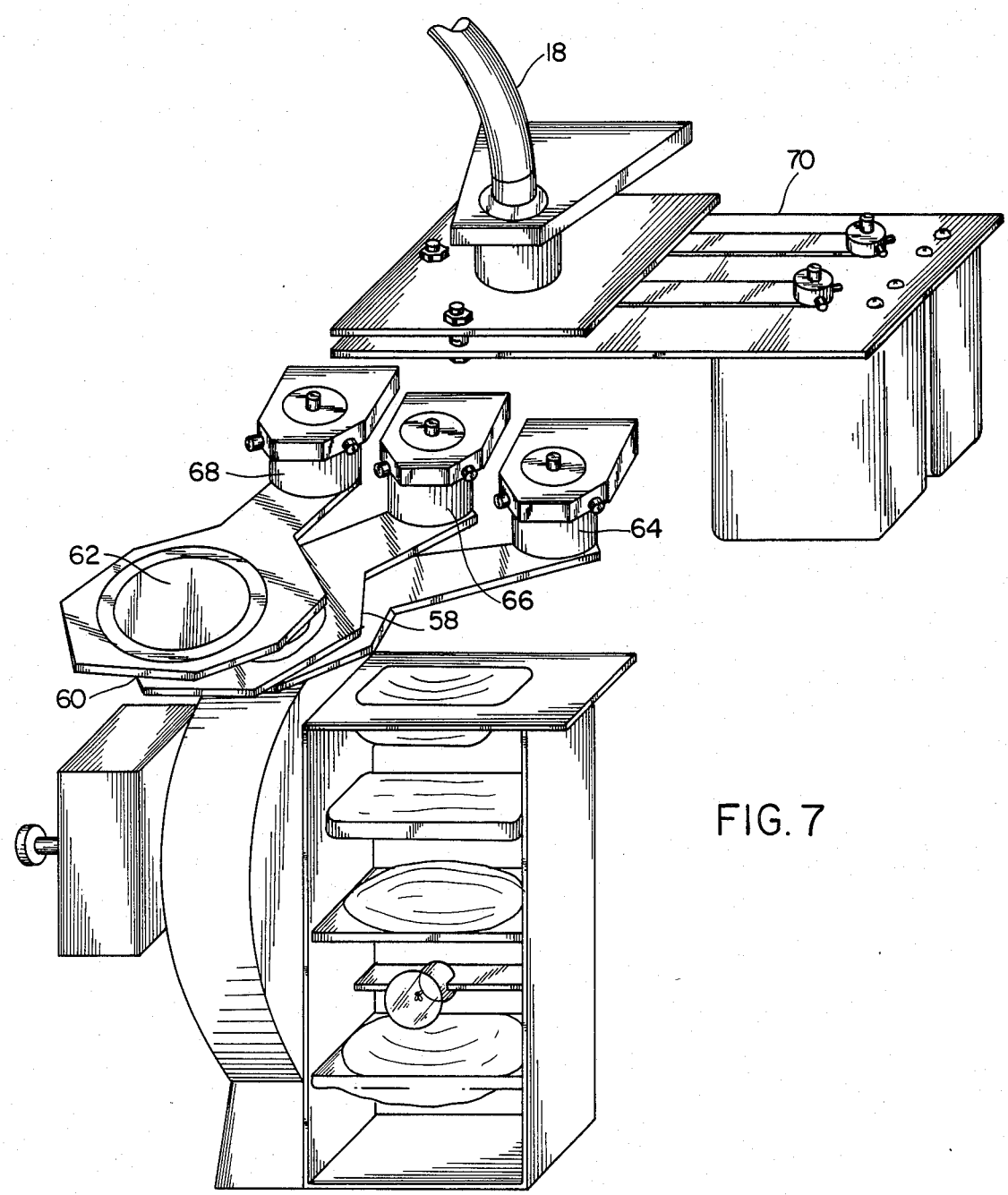
FIG. 7 is a pictorial representation of the optics portion of the flashlight section of the preferred embodiment.

FIG. 7 is a pictorial representation of the optics portion of the flashlight section of the preferred embodiment. The flashlight section includes a vertically mounted light source and associated condensing optics obtained from a Rollei P350A slide projector identical to that used in the background light section.

Three chromatic filters (red, blue and green) 58, 60 and 62 are pivotally mounted on electronically controllable rotary solenoids ("filter movement means") 64, 66 and 68 which may be electronically actuated as hereinafter described to pivot any of chromatic filters 58, 60 or 62 into or out of the light path between the flashlight section light source and fibre optics cable 18. This provides the operator with remote control over the chromatic filtration of light flashed into stimulator bowl 10.

The flashlight section also includes a light shutter 70 which is mounted above chromatic filters 58, 60 and 62 between a final converging lens 72 and fibre optics cable 18.

Figure 6:
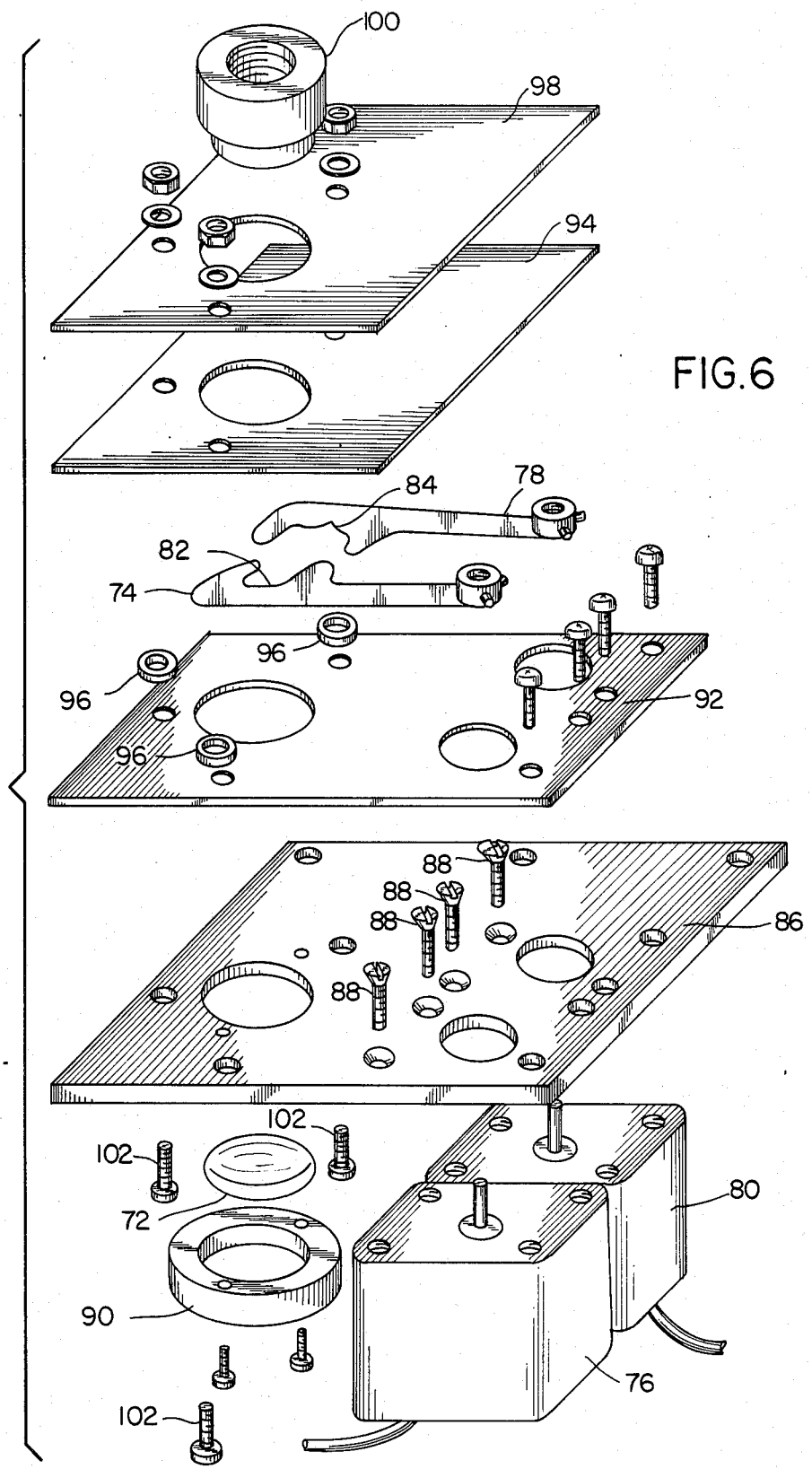
FIG. 6 is an exploded view of the light shutter used in the preferred embodiment.

FIG. 6 provides an exploded illustration of light shutter 70. A first shutter leaf 74 is rigidly affixed to the meter movement shaft of a first galvanometer 76. A second shutter leaf 78 is rigidly affixed to the meter movement shaft of a second galvanometer 80. The shutter leaves are positioned for pivotal movement with the galvanometer shafts to variably attenuate light passing between the shutter leaves, as hereinafter described.

A first notch 82 is cut in first shutter leaf 74 and a second notch 84 is cut in second shutter leaf 78. Shutter leaves 74 and 78 are positioned to define a light attenuating aperture between notches 82 and 84. Shutter leaves 74 and 78 are affixed on the shafts of galvanometers 76 and 80 such that, when no current passes through the galvanometers, shutter leaves 74 and 78 overlap one another, "closing" the aperture and preventing the passage of light between notches 82 and 84, thereby completely attenuating the flashlight source and preventing light from that source from reaching stimulator bowl 10 via fibre optics cable 18.

When current signals are applied to galvanometers 76 and 80, the galvanometer shafts pivot accordingly, causing shutter leaves 74 and 78 to pivot away from one another, "opening" the light attenuating aperture between notches 82 and 84, and enabling light to pass there-through. The arc through which each of shutter leaves 74 and 78 pivot, and the resultant aperture opening, are directly proportional to the magnitude of the current signals applied to galvanometers 76 and 80. The light flux allowed through the shutter is, in turn, directly proportional to the area of the aperture opening.

Notches 82 and 84 are shaped so that the area of the light attenuating aperture between shutter leaves 74 and 78 varies in proportion to the exponential of the distance between shutter leaves 74 and 78. This is accomplished, in the preferred embodiment, by giving first notch 82 a semi-circular shape and by giving second notch 84 a shape which converges in exponential fashion. The appropriate notch shape may be determined experimentally by measuring the attenuation of light passing through the aperture at various aperture settings, and then varying the shape of the notches as required so that the aperture area varies in proportion to the exponential of the distance between the shutter leaves. The effect is that, for relatively small aperture openings, the area of the aperture is proportional to the exponential of the distance shutter leaves 74 and 78 have moved apart. Accordingly, the attenuating effect of shutter 70, in dB, is approximately directly proportional to the degree of rotation of the galvanometer shafts. This allows light shutter 70 not only to interrupt the flashlight source (by selectably opening or closing the light attenuating aperture), but also to attenuate the flashlight source over a range of about zero to 40 dB.

Galvanometers 76 and 80 are mounted beneath a ⅛th inch thick aluminium plate 86 with the aid of screws 88. Final converging lens 72 is mounted on the bottom of plate 86 with the aid of lens holder 90. A 1/32nd inch thick stainless steel plate 92 is mounted on top of plate 86 to provide a wear-resistant surface for shutter leaves 74 and 78. Shutter leaves 74 and 78, which are cut from a piece of 0.005 inch thick stainless steel, move across the surface of plate 92. Another 1/32nd inch thick stainless steel plate 94 is mounted immediately above shutter leaves 74 and 78 with the aid of spacers 96. Plate 94 prevents vertical fluttering of shutter leaves 74 and 78. A 1/16th inch thick aluminium plate 98 is placed on top of plate 94 to provide a mounting surface for connector 100 to which fibre optics cable 18 is attached. Connector 100 also prevents stray light from bypassing the shutter. Stove bolts 102 and associated nuts and washers are used to hold plates 86, 92, 94 and 98 together.

IV. Stimulator Bowl

Stimulator bowl 10 is formed from plexiglass in a hemispherical shape and coated on the inside with Eastman Kodak No. 6080 white reflectance coating. Stimulator bowl 10 is supported from the rear on a yoke (not shown) which is mounted on a ball and socket joint and supported on a steel-pipe stand 104 manufactured by Life-Tech Instruments, Inc. of Houston, Tex. Optics box 22 is mounted on pipe stand 104 as shown in FIG. 1.

Fibre optics cables 16 and 18 convey light, respectively, from the background and flashlight sections of optics box 22 to stimulator bowl 10. Fibre optics cables 16 and 18 are connected to the bottom of stimulator bowl 10, adjacent to its outer rim, behind reflector 106 which disperses light evenly over the inner surface of stimulator bowl 10.

A solid-state photo diode 108 is mounted in stimulator bowl 10 on top of head rest 14 to detect radiant energy directed into the subject's eyes from stimulator bowl 10. Photo diode 108 produces a "first" output signal representative of the radiant energy directed into the subject's eyes for processing as hereinafter described.

A pair of red light emitting diodes 110, 112 are mounted in the back of stimulator bowl 10 to facilitate EOG testing as hereinafter described.

V. Control Console

Figure 2A:
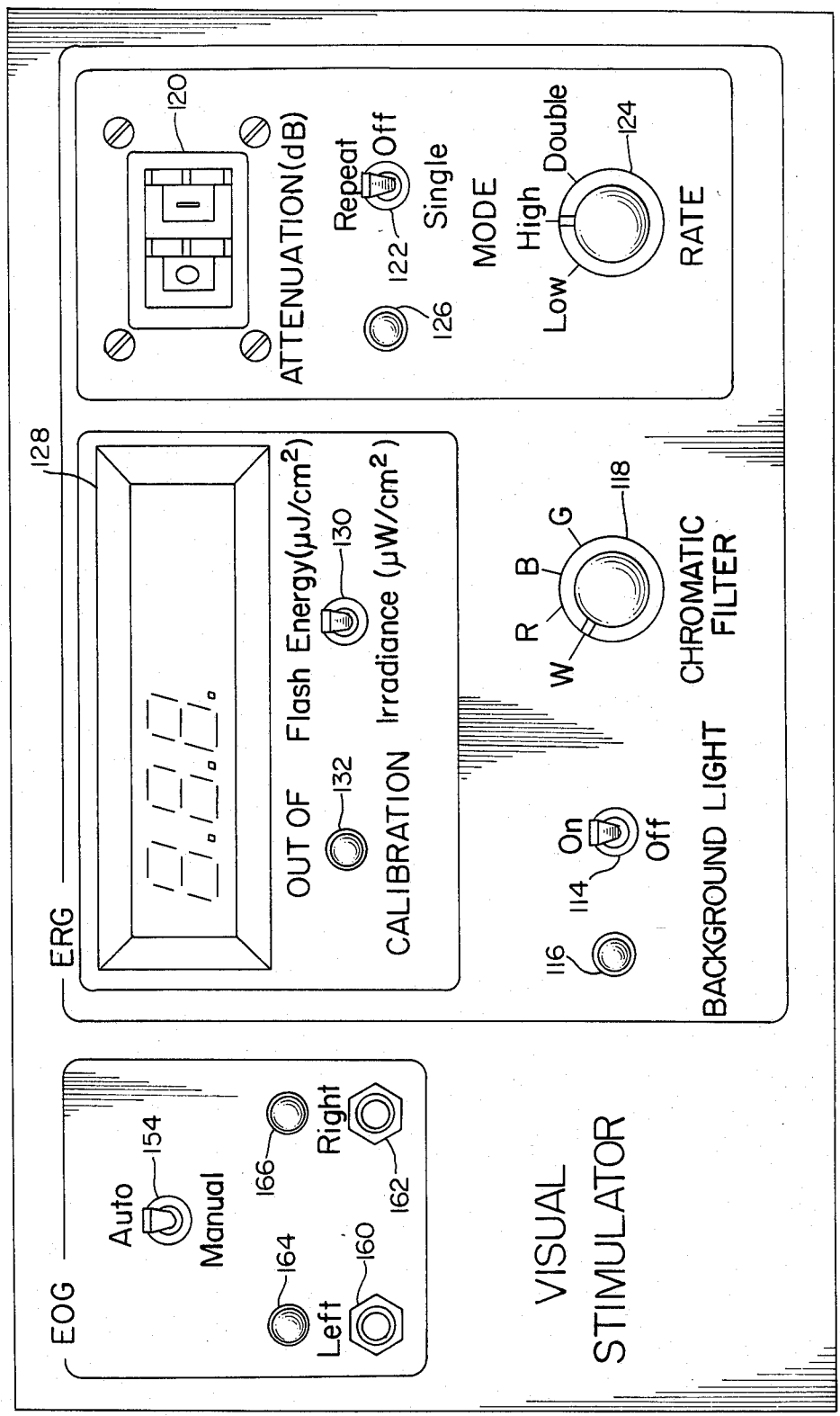
FIGS. 2a and 2b are, respectively, pictorial representations of front and back panels for the control console of the preferred embodiment.
Figure 2B:
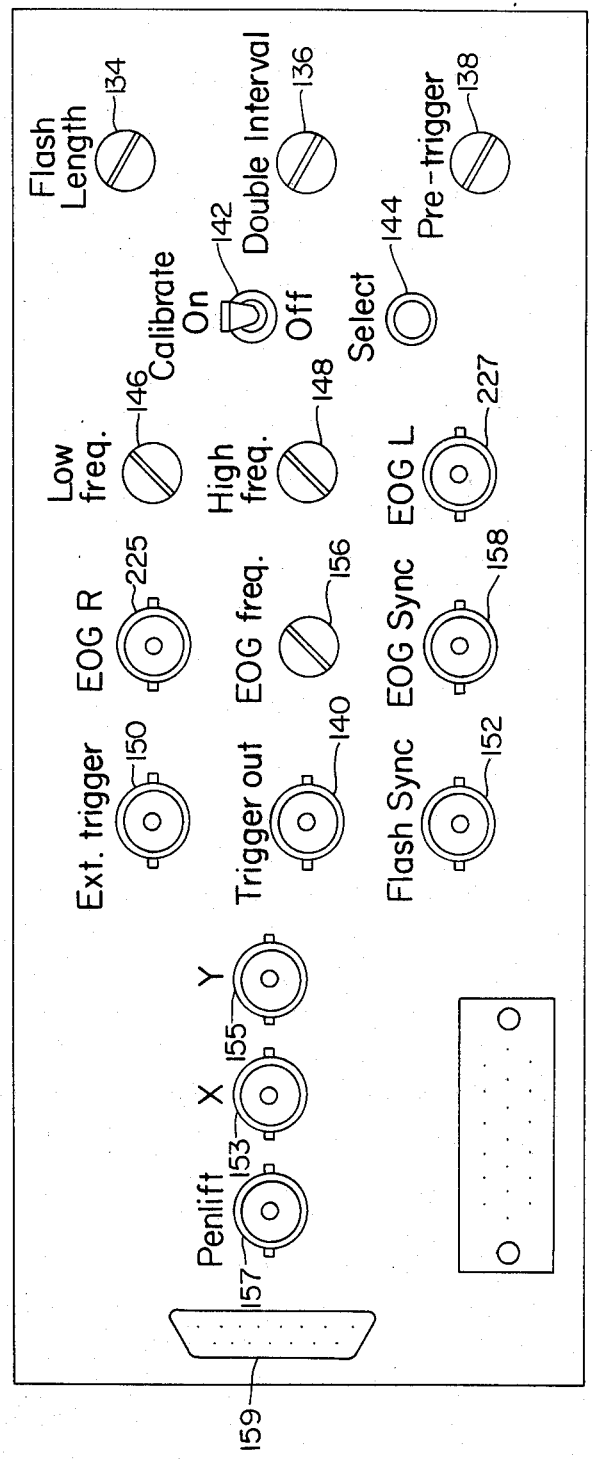

FIGS. 2a and 2b are, respectively, pictorial representations of the front and back panels of control console 20.

The front control panel (FIG. 2a) is divided into two separate segments labelled, respectively, "ERG" and "EOG". The segment labelled "ERG" may be used to control the visual stimulator when ERG measurements are to be obtained, or when flash VEP measurements are desired. The segment labelled "EOG" may be used to control the visual stimulator when EOG measurements are to be obtained.

A switch 114 is provided for turning background lightbulb 24 on or off. Light emitting diode 116 is turned on when switch 114 is in the "on" position to provide the operator (who may be separated from the subject and from stimulator bowl 10) with a visual indication of whether the background light source is on or off.

A four-position switch 118 serves as a filter position selection means with which the operator may select one of chromatic filters 58, 60 or 62 for positioning in the light path between the flashlight section light source and fibre optics cable 18 to chromatically filter the flashlight source. The four positions of switch 118 are marked, respectively, "W", "R", "B" and "G" corresponding, respectively, to white (i.e. no) chromatic filtering, red chromatic filtering (i.e. rotary solenoid 64 is actuated to position red chromatic filter 58 in the light path between the flashlight section light source and fibre optics cable 18), blue chromatic filtering and green chromatic filtering.

A pair of thumb-wheel switches 120 are calibrated, as hereinafter described, to control the attenuation of the flashlight section light source by enabling the application of selected current signals to galvanometers 76 and 80, thereby selectably pivoting shutter leaves 74 and 78 to vary the opening of the light attenuating aperture between the leaves. Thumb-wheel switches 120 are calibrated to read off directly in dB, with a dynamic range of zero through 39 dB, corresponding to the 40 dB attenuation capability of light shutter 70.

A three-position switch 122 permits the operator to trigger the flashlight section light source to produce either a single flash sequence, or a repetition of flash sequences in stimulator bowl 10. For example, by depressing switch 122 from its normal "off" position to the "single" position, the operator will cause shutter leaves 74 and 78 to pivot apart (the degree of pivoting, and the resultant attenuation being determined by the setting of thumb-wheel switches 120), thus triggering a single light flash, or flash pair, in stimulator bowl 10. By holding switch 122 in the "repeat" position, the operator will cause shutter leaves 74 and 78 to repeatedly pivot apart and close, thus repeatedly interrupting the flashlight source and illuminating stimulator bowl 10 with a series of flash sequences.

The rate at which flashes are produced when switch 122 is in the "repeat" position may be controlled by the operator with the aid of three-position switch 124. When switch 124 is in the "low" position, the flash repetition rate may be varied from 0.2 to 2 Hertz by adjusting low frequency trimpot 146 (FIG. 2b). When switch 124 is in the "high" position, the flash repetition rate may be varied from 27 to 33 Hertz by adjusting hugh frequency trimpot 148 (FIG. 2*b*). When switch 124 is in the "double" position, two flashes are sent in rapid succession, the time interval between successive flashes being determined by the setting of double interval adjustment trimpot 136 (FIG. 2*b*) as hereinafter described, and the frequency of the flash pair being dependant upon the setting of low frequency trimpot 146.

When switch 124 is in either the "low" or "double" positions, a pre-trigger pulse is output from pre-trigger BNC jack 140 (FIG. 2*b*) immediately before the flash, to allow triggering of a signal averaging device before the flash occurs. The length of the pre-trigger pulse may be adjusted with the aid of pre-trigger trimpot 138 (FIG. 2*b*) as hereinafter described. When switch 124 is in the "high" position, no pre-trigger pulse is sent and the flash length is held constant at 15 milliseconds.

The flashlight section lightbulb is controlled by electronic circuitry in order to minimize "on" time and therefore prolong its life. This may sometimes cause a slight delay of the flash. For example, when switch 122 is actuated for the first time after the apparatus has been turned on, the actual triggering of the flashlight section lightbulb is delayed for about one second to allow the lightbulb to turn on and reach its full intensity. Subsequent actuation of switch 122 should cause immediate illumination of stimulator bowl 10 by the flashlight section lightbulb, unless more than about five minutes have elapsed since the last flash. The flashlight section lightbulb is automatically switched off if light shutter 70 is not triggered for at least five minutes to produce a light flash in stimulator bowl 10.

A green light emitting diode 126 is illuminated for the full duration of each flash to give the operator a quick visual check on the flash frequency and duration. Since the operator is often separated from the subject and from the stimulator bowl, this feature may be of considerable assistance to the operator.

Display 128 includes a three-digit, seven-segment light emitting diode display for providing the operator with an indication of the photometric or radiometric characteristics of the flash radiant energy, such as the irradiance in stimulator bowl 10 (in microwatts per square centimeter) or the radiant or illuminance energy of the last flash used to illuminate stimulator bowl 10 (in microjoules per square centimeter). A two-position switch 130 permits the operator to select the measurements appearing in display 128 by moving the switch between the "flash energy" and "irradiance" positions.

Light emitting diode 132 is illuminated if the light flux detected at photo diode 108 differs, for three successive flashes, from the expected light flux, by more than a pre-selected amount. Illumination of light emitting diode 132 constitutes an alarm signal to notify the operator that the apparatus is out of calibration. Light emitting diode 132 is extinguished as soon as the light flux detected at photo diode 108 does not deviate from the expected light flux by more than a pre-selected amount.

Flash length adjustment trimpot 134 (FIG. 2*b*) facilitates adjustment of the flash length from 10 to 320 milliseconds in 10 millisecond steps. Double interval adjustment trimpot 136 facilitates adjustment of the time interval between flash pairs (produced when flash rate switch 124 is in the "double" position) from 100 to 730 milliseconds in 10 millisecond steps. Pre-trigger interval adjustment trimpot 138 facilitates adjustment of the length of the pre-trigger interval pulse (output at BNC jack 140) from 10 to 80 milliseconds in 10 millisecond steps.

Trimpots 134, 136 and 138 are enabled only when calibration switch 142 is moved from its normal "off" position into the "on" position. When calibration switch 142 is in the "on" position, calibration selection pushbutton 144 may be depressed to select one of trimpots 134, 136 or 138. When calibration switch 142 is in the "on" position, one of the messages "flash length", "double interval" or "pre-trigger interval" will be displayed at the right side of display 128, depending upon which of trimpots 134, 136 or 138 has been selected with the aid of calibration selection push-button 144. For example, the message "flash length" appears at the right side of display 128 if calibration selection push-button 144 has been depressed to enable flash length adjustment trimpot 134. In this case, the three-digit, seven-segment portion of display 128 provides the operator with a visual reading of the flash length in milliseconds. After adjusting the flash length with the aid of trimpot 134, the operator may then depress calibration selection push-button 144 once, to enable double interval adjustment trimpot 136. This will be indicated by the appearance of the message "double interval" in the right portion of display 128. In this case, the three-digit, seven-segment portion of display 128 provides a readout, in milliseconds, of the time interval between successive flash pairs. After adjusting that time interval with the aid of trimpot 136, the operator may again depress calibration selection push-button 144 once to enable pre-trigger interval adjustment trimpot 138. This will be indicated by the appearance of the message "pre-trigger interval" in the right portion of display 128. In this case, the three-digit, seven-segment portion of display 128 provides a readout, in milliseconds, of the length of the pre-trigger pulse, which may be adjusted with the aid of trimpot 138.

Adjustment of any of trimpots 134, 136 or 138 when calibration switch 142 is in the "off" position has no effect, unless the visual stimulator apparatus is turned off and on again. This is because the settings of trimpots 134, 136 and 138 are "read" only when the apparatus is first turned on, or when calibration switch 142 is in the "on" position.

BNC jack 150 facilitates connection of external devices for triggering the visual stimulator. Application of a voltage potential of between 2.0 and 25 volts at jack 150 will trigger the flashlight section to produce a flash or flash sequence in stimulator bowl 10 according to the settings of switches 120, 122 and 124. The voltage potential at jack 150 should not exceed 30 volts (to avoid damaging voltage comparator 246 hereinafter described) or a frequency of 50 Hertz (since this frequency approaches the limit of the light shutter's mechanical capability).

A 0.1 volt signal is presented across the terminals of BNC jack 152 whenever light shutter 70 is opened. This signal may be recorded concurrently with the subject's ERG response, etc. for correlation of the are routinely used in ERG testing to average and amplify ERG response with the opening of the shutter.

BNC jacks 153, 155 and 157 facilitate coupling the apparatus to the "X", "Y" and "penlift" output ports of a conventional signal averaging device. Such devices are routinely used in ERG testing to average and amplify ERG response signals obtained from the subject and to drive an X-Y plotting device to produce a graphical representation of the ERG waveform by plotting electrical potential (in uV) as the ordinate versus time (in milliseconds) as the abscissa. By continually monitoring the signal at "penlift" port 157, the software which controls the operation of the preferred embodiment may determine whether or not any plotting is to be done. Analog data passed from the "X" and "Y" ports of the signal averaging device is digitized by the visual stimulator apparatus and then passed to a plotting device (not shown) via RS232 connector 159. In addition to digitizing the data, the visual stimulator apparatus determines the maxima and minima of the ERG waveform and flags them with special symbols on the graph plotted on the plotting device. The visual stimulator apparatus also calculates the difference (in uV) between the maxima and minima of the ERG waveform and prints that value on the graph plotted on the plotting device. The time interval (in milliseconds) between the start of the light flash and attainment of the ERG waveform maximum is also calculated and printed on the graph. The attenuation (in dB), flash length (in milliseconds), chromatic filtering ("white", "red", "blue" or "green"), calibration status ("OK" or "error") and time the flash occurred (with respect to the time axis of the graph) are also annotated on the graph to produce a one-page documentary summary of the ERG test.

The "EOG" segment of control console 20 provides both "manual" and "automatic" modes of operation which are selected with the aid of two-position switch 154. EOG electrodes attached to the subject are coupled to the apparatus (through external amplifiers—not shown) via BNC jacks 225 and 227 (FIG. 2b).

When switch 154 is in the "auto" position, EOG light emitting diodes 110 and 112 in stimulator bowl 10 (FIG. 1) are alternately illuminated and extinguished over five EOG cycles in each minute of a 30-minute time span. The EOG cycle frequency may be varied from 0.2 to 2 Hertz by adjusting EOG rate trimpot 156 (FIG. 2b). The first 15 minutes of the test is conducted in dark adapted conditions (i.e. background lightbulb 24 is off) and the last 15 minutes of the test is conducted in light adapted conditions (i.e. background lightbulb 24 is on).

The apparatus determines, in respect of the previously mentioned five EOG cycles of each minute during the 30-minute span, the amplitude of the EOG waveform and stores that value in a memory device. At the end of the 30-minute span a hard-copy record is produced on an X-Y plotting device (not shown) via RS232 connector 159 (FIG. 2b) by plotting the EOG amplitude (in uV) as the ordinate versus time (in minutes) as the abscissa. Separate traces are plotted for each eye, on the same sheet of paper. The apparatus also determines and prints on the graph, the light rise ratio which is the peak amplitude during light adaptation divided by the lowest amplitude during dark adaptation. Accordingly, a compact record of each EOG testing session is produced, which simplifies analysis of the results.

A TTL compatible square wave signal synchronized with the EOG light frequency is provided at the output of BNC connector 158 (FIG. 2b) for use in monitoring EOG tests.

When switch 154 is in the "manual" position, EOG light emitting diodes 110 and 112 are illuminated only if either of push-buttons 160 or 162 are pressed. Pressing "left" push-button 160 forces the left hand EOG light emitting diode 110 "on" for as long as the button is held down, regardless of the position of switch 154. Similarly, pressing "right" push-button 162 forces the right hand EOG light emitting diode 112 "on" regardless of the position of switch 154. Light emitting diodes 164 and 166 are illuminated, respectively, whenever EOG light emitting diodes 110 or 112 are illuminated, providing the operator with a visual indication of the status of the EOG light emitting diodes 110 and 112.

VI. Attenuation Calibration of Light Shutter

Light shutter 70 is actuated, as hereinafter described, with the aid of an eight bit digital to analog converter. Accordingly, there are 256 possible settings for the area of the light-attenuating aperture defined by notches 82 and 84 in shutter leaves 74 and 78. The numbers zero through 255 may thus be used to represent the possible range of aperture settings. To calibrate attenuation thumb-wheel switches 120, one of the possible 256 shutter settings must be selected to correspond to each of the 40 possible positions of thumb-wheel switches 120 (thumb-wheel switches 120 may be positioned to show the numbers from zero through 39 to define the 40 possible settings which correspond to the 40 dB attenuation capability of light shutter 70). Calibration of switches 120 should only be necessary if characteristics of the flashlight section light pathway or of the electronic circuitry controlling light shutter 70 change. It may, for example, be necessary to recalibrate switches 120 if stimulator bowl 10 is recoated, if shutter leaves 74 and 78 are removed from galvanometers 76 and 80, if any electronic components in the shutter control circuitry or power supplies are changed, etc. Calibration may be done manually or automatically.

Before entering the automatic calibration mode, the operator should eliminate any sources of ambient light in the vicinity of stimulator bowl 10 so that the calibration will be done at zero background irradiance. Automatic calibration is initiated by moving calibration switch 142 (FIG. 2b) to the "off" position and then depressing and holding down calibration selection push-button 144. The numerals "000" (representing the initial attenuation setting of 0 dB corresponding to a wide open aperture) are initially displayed in display 128 and the apparatus waits until the irradiance measured in stimulator bowl 10 equals zero. Once a zero irradiance value is detected the apparatus cycles through the range of possible attenuation settings, triggering light shutter 70 and measuring the resultant radiant energy in stimulator bowl 10 at each attenuation setting. The current attenuation setting, in dB, is displayed in display 128.

If the light flux detected at photo diode 108 differs, at a given aperture setting, and for three successive flashes, by more than a pre-selected amount from the expected light flux, then the apparatus searches for a different aperture setting which will yield the expected light flux. When the appropriate aperture setting is found, it is stored in a calibration table maintained in a memory device. Automatic calibration continues in similar fashion for each possible aperture setting, and may be aborted at any time by releasing calibration selection push-button 144. Automatic calibration facilitates simple, rapid calibration of the apparatus to compensate for changed optical conditions such as lightbulb decay, movement of the various lenses, wear of shutter leaves 74 and 78, etc.

The manual attenuation calibration mode facilitates complete external calibration of the device. To enter the manual attenuation calibration mode, calibration switch 142 must be toggled at a rate slightly less than 0.5 Hertz. Since normal operation of the visual stimulator apparatus should never call for such toggling of switch 142, inadvertant entry of the manual attenuation calibration mode should be avoided. Light emitting diode 132 remains "on" throughout the duration of the manual attenuating calibration mode.

When the manual attenuation calibration mode is first entered, and provided switch 130 is in the "irradiance" position, the three-digit, seven-segment portion of display 128 provides a visual indication of the present attenuation calibration setting for each position of thumb-wheel switches 120 (i.e. a number between zero and 255 appears in display 128 for each of the 40 possible positions of thumb-wheel switches 120, depending upon the previous calibration). Moving switch 130 to the "flash energy" position causes the radiant flash energy of the last light flash which illuminated stimulator bowl 10 to be displayed (in microjoules per square centimeter) in the three-digit, seven-segment portion of display 128.

Calibration switch 142 and calibration selection push-button 144 are used to change the calibration settings of thumb-wheel switches 120. Calibration switch 142 is moved to the "on" position if it is desired to change the attenuation calibration setting appearing in display 128 to a higher value, or to the "off" position if it is desired to change the attenuation calibration setting to a lower value. Calibration selection push-button 144 is then pressed to change the attenuation calibration value. The attentuation calibration value changes relatively slowly for the first four counts and then relatively rapidly thereafter. The operator may, at any time, use flash trigger switch 122 to produce a light flash within stimulator bowl 10 in order to obtain a measurment of the radiant energy at the current attenuation calibration setting. The manual attenuation calibration mode may be exited at any time by again toggling calibration switch 142 at a rate slightly less than 0.5 Hertz.

A typical manual attenuation calibration session may accordingly proceed as follows:

(1) Adjust the flash length to the desired value with the aid of flash length trimpot 134 since it cannot later be changed during the manual attenuation calibration sequence.

(2) Enter the manual attenuation calibration mode by toggling calibration switch 142 at slightly less than 0.5 Hertz.

(3) Move display selector switch 130 to the "irradiance" position to cause attenuation calibration settings to appear in the three-digit, seven-segment portion of display 128.

(4) Adjust thumb-wheel switches 120 to the "00" position (corresponding to an attenuation of 0 dB). The value "255" should appear in display 128 corresponding to a "wide open" setting of light shutter 70 and no attenuation of the flashlight source.

(5) Produce a light flash in stimulator bowl 10 with the aid of flash trigger switch 122 and use an accurate radiometer to measure the radiant energy of that flash.

(6) Adjust thumb-wheel switches 120 to the "01 dB" position and experiment with different attenuation calibration settings until the radiant energy of flashes produced in stimulator bowl 10 is 1 dB down from the radiant energy of flashes produced at the previous attenuation setting of switches 120.

(7) Repeat step 6 by advancing switches 120 through all 40 possible settings.

(8) Exit the manual attenuation calibration mode by toggling calibration switch 142 at a rate slightly less than 0.5 Hertz.

VII. Microprocessor and Electronic Circuitry

An Intel 8085 microprocessor (FIG. 5) controls the electronic circuitry in the preferred embodiment. Three Intel 2732 erasable programmable read only memories ("EPROM") 170, 172 and 173; two Intel 2142 static random access memories ("RAM") 174 and 176; and two Xicor X2210 electronically erasable programmable read only memories ("EEPROM") 178 and 180 are used to store the logic programs defining the sequence of operations by which microprocessor 168 controls the operation of the visual stimulator and to store volatile data. (The aforementioned attenuation calibration tables are maintained in EEPROMs 178 and 180. Accordingly, since these devices are capable of retaining data when power is switched off, the attenuation calibration tables are not lost when the power is switched off.) A National Semiconductor 74LS138 memory select integrated circuit 182 facilitates selection of the memory devices as follows:

| Address Range (Hexadecimal) | Memory Device |
|---|---|
| 0–0FFF | EPROM 170 |
| 1000–1FFF | EPROM 172 |
| 2000–2FFF | EPROM 173 |
| 3000–33FF | RAMs 174 and 176 |
| 4000–403F | EEPROMs 178 and 180 |

An Intel 8212 latch integrated circuit 184 is used to latch the lower eight bits of the address bus from data-/address bus 186 at the falling edge of the address latch enable ("ALE") signal produced by microprocessor 168.

Figure 5A:
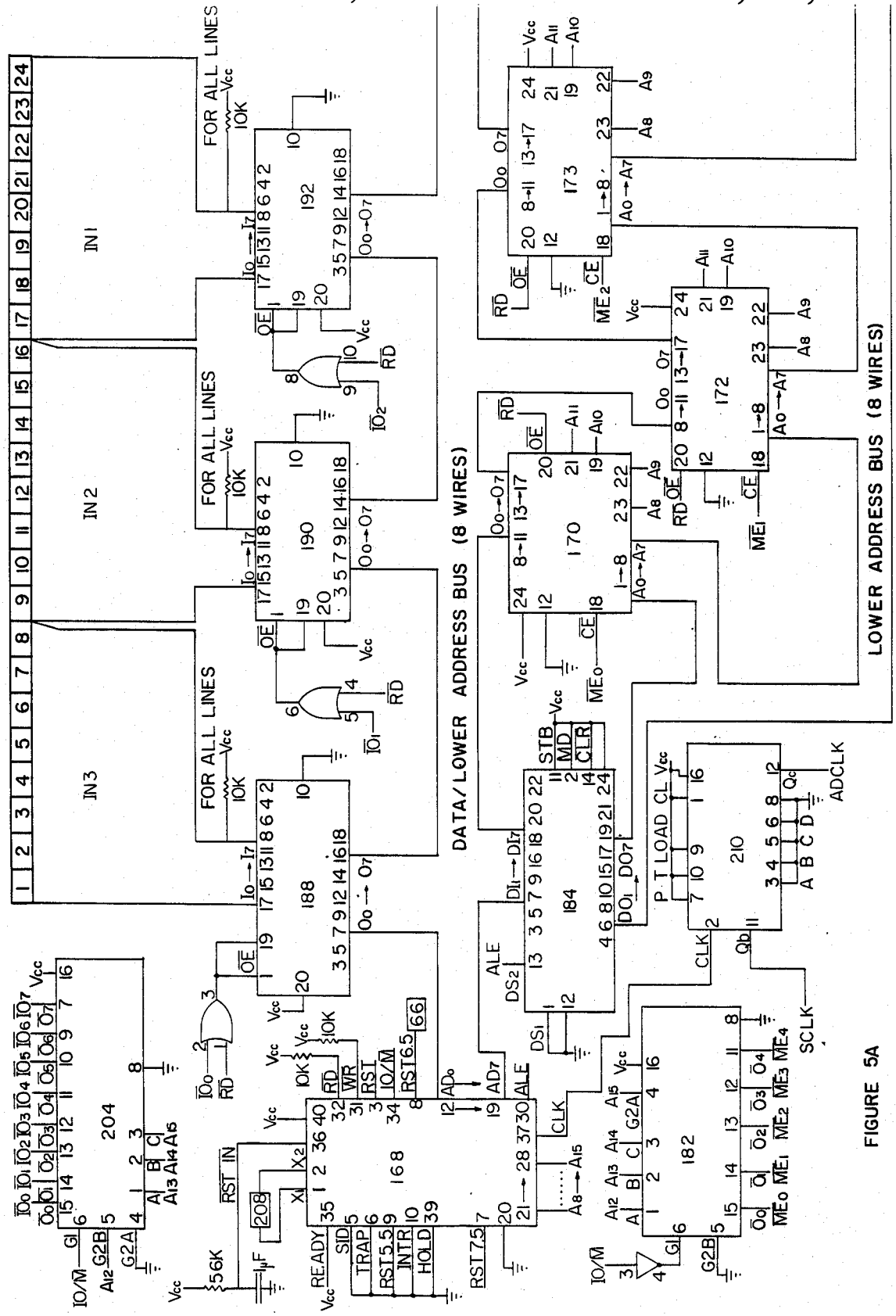
FIGS. 5a and 5b (hereinafter collectively called "FIG. 5") together comprise an electronic circuit schematic diagram for the microprocessor and related circuitry of the preferred embodiment.
Figure 5B:
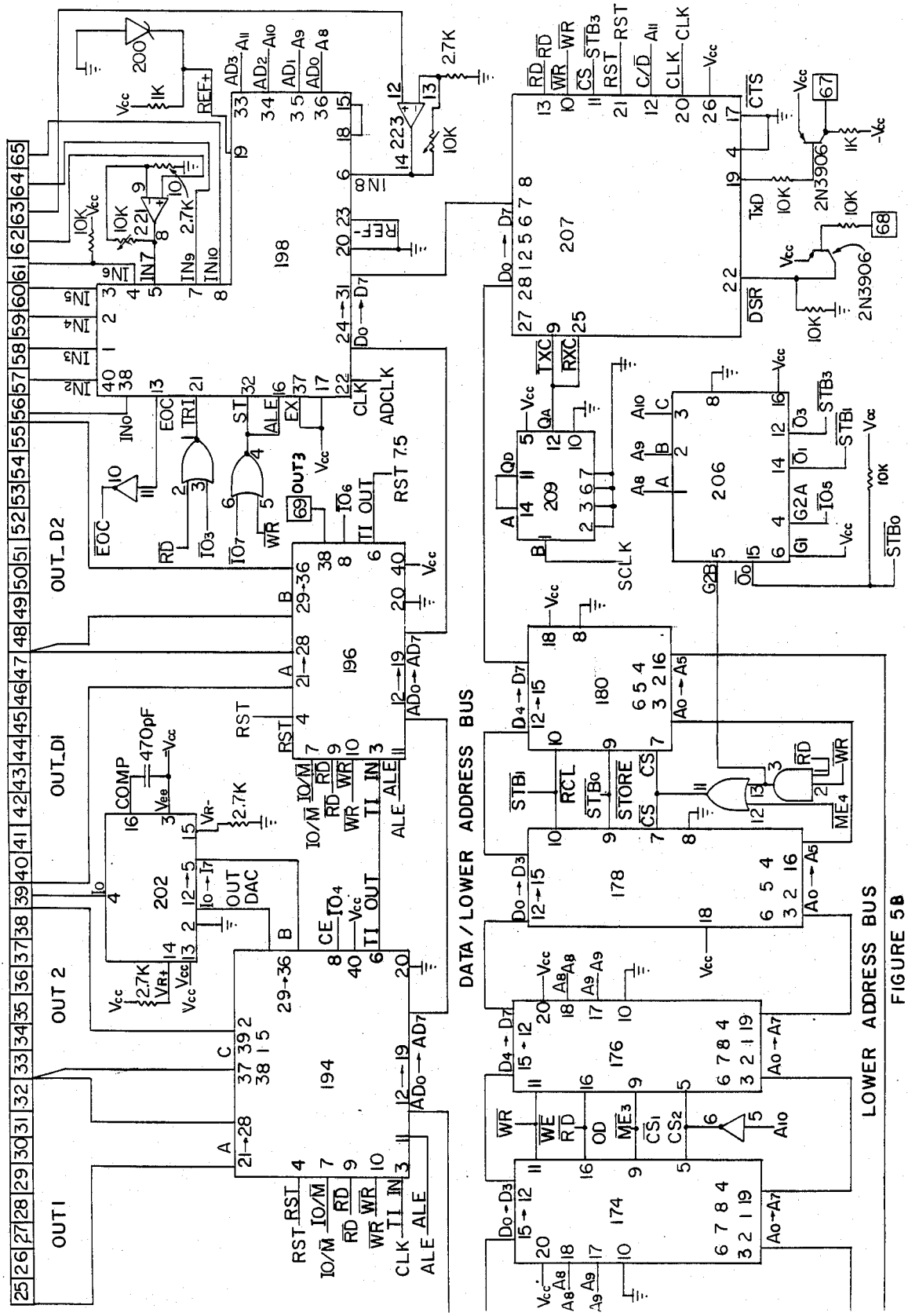

Input/output ("I/O") operations are handled by the integrated circuitry depicted above data bus 186 in FIG. 5. 10k ohm pull-up resistors are used on all digital inputs to microprocessor 168. Such inputs are gated with the aid of Motorola 74LS244 tri-state buffers 188, 190 and 192. The five eight-bit digital output ports "OUT1", "OUT2", "OUT3", "OUTD1" and "OUTD2" are latched by Intel 8155 integrated circuits 194 and 196.

A National Semiconductor ADC0816 analog to digital converter 198 converts analog voltage signals in the 0 to 3.6 volt range into digital format. A 1N4729 zener diode 200 defines the 0 to 3.6 volt input range of analog to digital converter 198. This ensures maximum quantization of the 0 to 3.5 volt output range of the National Semiconductor LM324 operational amplifiers hereinafter described. The analog output is accomplished by a National Semiconductor DAC0808 digital to analog converter 202 which is driven by one of the output ports. A second National Semiconductor 74LS138 shown at 204 in FIG. 5 is used to select the appropriate I/O chips during an I/O operation.

A National Semiconductor 74LS138 integrated circuit shown at 206 in FIG. 5 is used to produce a 400 nanosecond pulse when an I/O "read" or "write" occurs to locations A0 through A7 (which are dedicated to the performace of I/O functions by the specific microprocessor used in the preferred embodiment). This pulse enables storage and recall of data from the memory devices under software control.

Microprocessor 168 is driven at three megahertz with the aid of a 6.144 megahertz crystal 208. Clock pulses for triggering analog to digital converter 198 are obtained by dividing the "CLK" output signal produced by microprocessor 168 by eight with the aid of National Semiconductor 74LS161 divider 210.

An Intel 8251A integrated circuit shown at 207 in FIG. 5 produces serial data output which gates a N3906 switching transistor to produce an RS232 ±5 volt output signal for driving a plotter via RS232 connector 159. Clock signals for driving integrated circuit 207 are obtained from integrated circuit divider 10 and further divided by a National Semiconductor 74LS90 divide-by-10 integrated circuit 209.

Figure 4A:
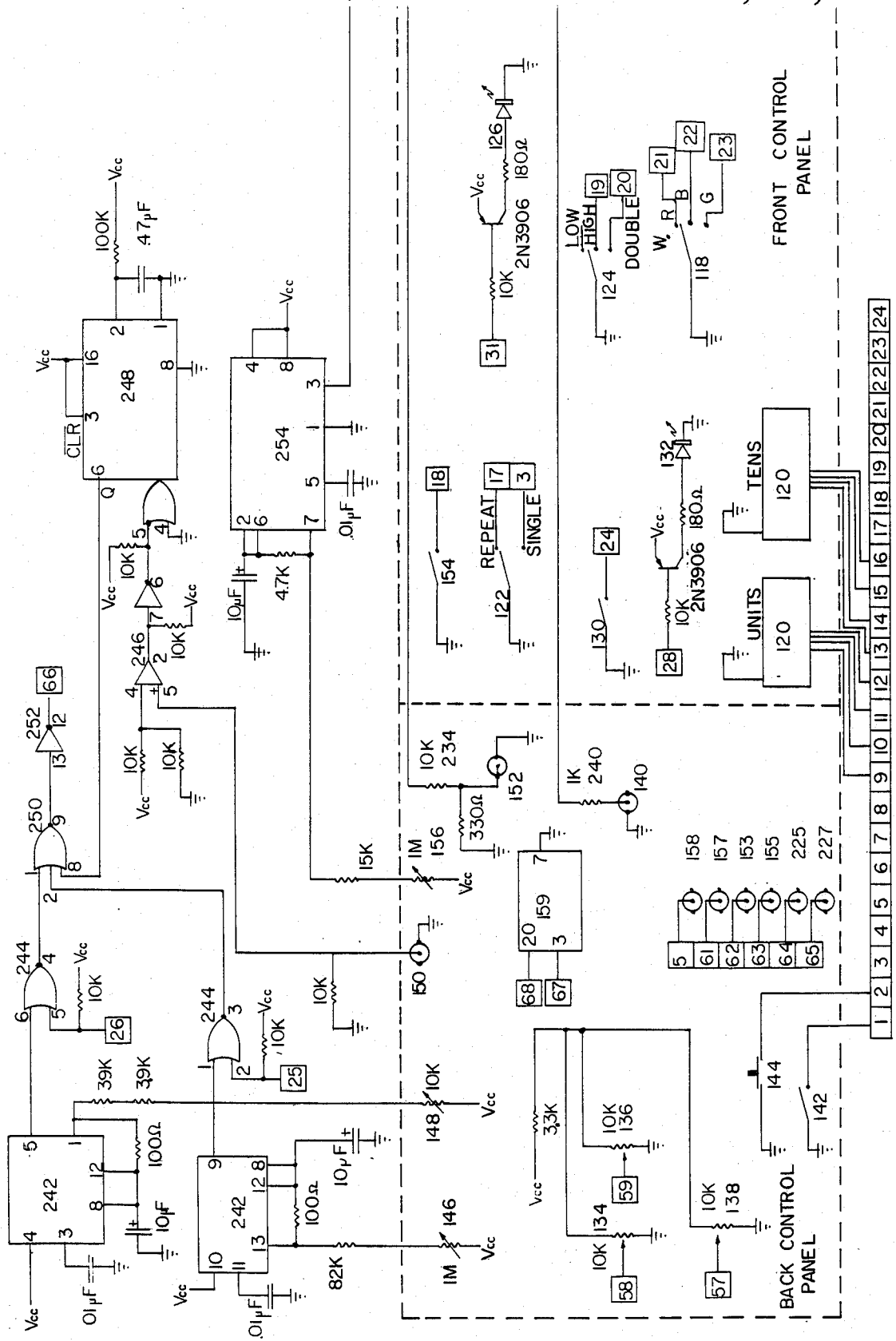
FIGS. 4a and 4b (hereinafter collectively called "FIG. 4") together comprise an electronic circuit schematic diagram for the control/display circuitry of the preferred embodiment.
Figure 4B:
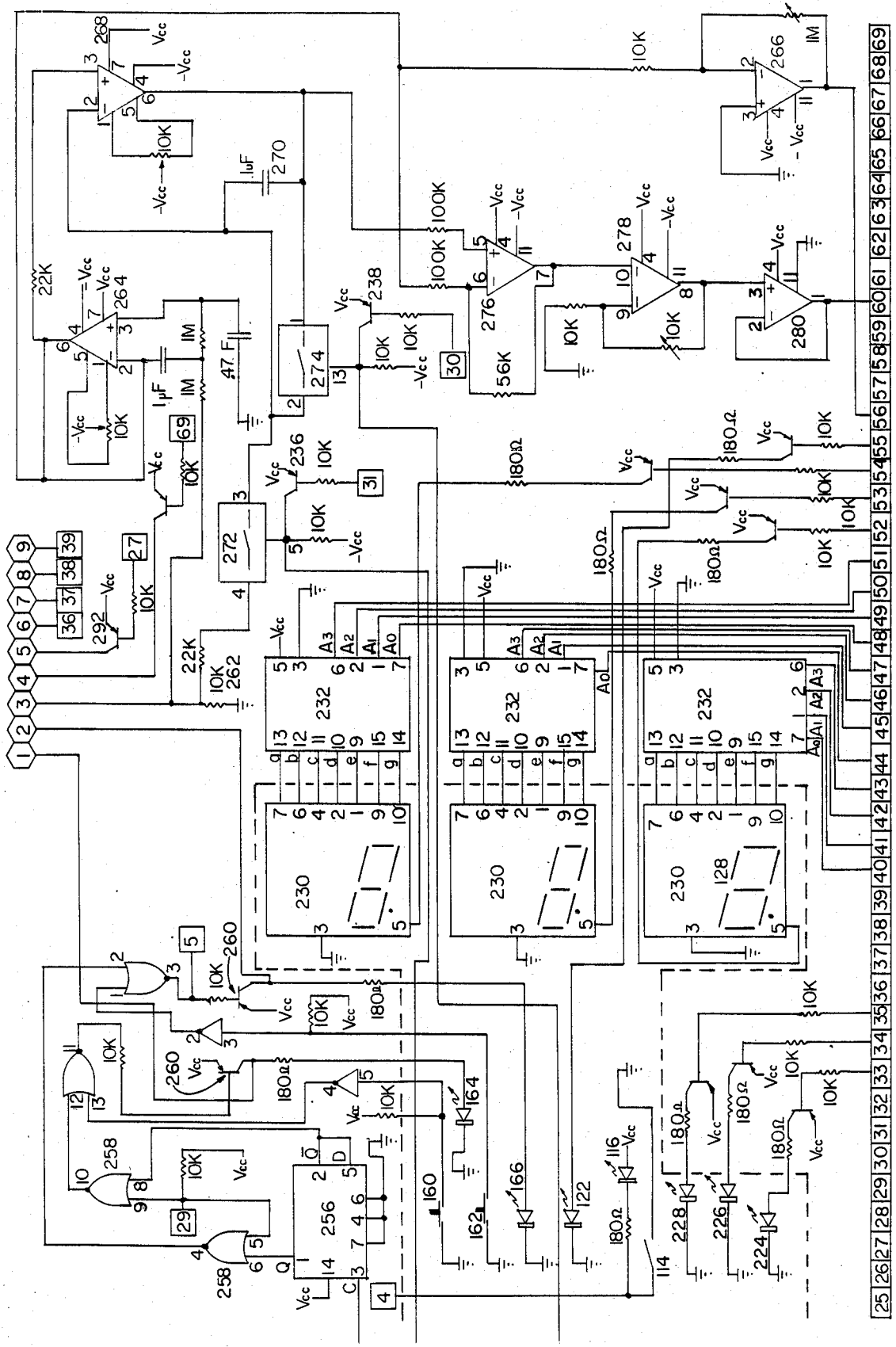

Connector 212 couples microprocessor 168 and its related circuitry to the control panel circuitry shown in FIG. 4 with the aid of mating connector 214.

Most of the signals obtained from the switches on control console 20 are fed directly to microprocessor 168 via the I/O circuitry shown in FIG. 5 above data base 186. An exception is the "left" and "right" EOG push-buttons 160 and 162 which directly gate light emitting diode pairs 110/164 and 112/166.

Calibration trimpots 134, 136 and 138 yield voltages in the range of 0 to 3.6 volts which are fed, respectively, into channels 3, 4 and 2 of analog to digital converter 198.

The input signal at "penlift" BNC jack 159 is directly input to channel 6 of analog to digital converter 198. The input signals at "X" and "Y" BNC jacks 155 and 157 are input, respectively, to channels 7 and 8 of analog to digital conveter 198 via National Semiconductor LM324 operational amplifiers 221 and 223. The output signals produced by EOG electrodes applied to the subject are input, respectively, (through external amplifiers—not shown) via BNC jacks 225 and 227 (FIG. 2b) to channels 9 and 10 of analog to digital converter 198.

Light emitting diodes 126 and 132 have a current limiting 180 ohm resistor driven by a 2N3906 switching transistor. The decimal points of the three-digit, seven-segment digital display 128 are driven in the same manner, with a discrete light emitting diode 222 used to provide the fourth decimal point to facilitate the display of numbers in the range "0.001" through "0.009". Light emitting diodes 224, 226 and 228 are placed behind message cutouts positioned in the right hand portion of display 128 to illuminate the messages during calibration with the aid of trimpots 134, 136 and 138. Three General Instrument MAN6780 seven-segment light emitting diode displays are used in display 128. Three Fairchild 9368 decoder-driver integrated circuits 232 with on-board current limiting are used to power light emitting diodes 230.

BNC jack 152 is coupled to a resistive potential divider 234 used to obtain a 0.1 volt signal with the aid of a 2N3906 drive transistor 236 which is software gated. "Pre-trigger" BNC jack 140 is driven by a 2N3906 drive transistor which is also gated by software. A 1k ohm current limiting resistor 240 is placed between drive transistor 238 and BNC jack 140.

Only the "RST 6.5" and "RST 7.5" interrupts of microprocessor 168 are used. The two clock signals for the RST 6.5 interrupt are provided by a National Semiconductor 556 integrated circuit shown at 242 in FIG. 4. Low frequency trimpot 146 and high frequency trimpot 148 facilitate adjustment of the clock frequencies provided by each half of integrated circuit 242. The clock output signals provided by each half of integrated circuit 242 are gated through Motorola 4001 NOR gates 244 to facilitate software selection of the RST 6.5 interrupt frequency. BNC jack 150 facilitates connection of an external device to trigger the RST 6.5 interrupt and consequently the flashes produced in stimulator bowl 10. The signal from BNC jack 150 is fed into a National Semiconductor LM339 voltage comparator integrated circuit 246 having a threshold of 2.5 volts determined by a resistor divider. Increasing the input voltage over the 2.5-volt threshold causes the presentation of a falling edge to Motorola 4528 monostable multivibrator 248 which, in turn, produces a controlled pulse of about 10 milliseconds duration. The two clock signals produced by the two halves of integrated circuit 242 and the pulse produced by monostable multivibrator 248 are "OR'd" by a Motorola 4025 NOR gate 250 and a Motorola 4049 integrated circuit inverter 252 for input to the "RST 6.5" input terminal of microprocessor 168. The RST 7.5 interrupt is clocked every minute by the "CLK" signal produced by microprocessor 168 which is in turn subdivided by two software controlled Intel 8155 timers 194, 196 before presentation to the "RST 7.5" interrupt terminal of microprocessor 168.

The frequency of EOG lights 110 and 112 is determined by a National Semiconductor 555 integrated circuit configured as an astable multivibrator, shown at 254 in FIG. 4. The EOG frequency may be adjusted from 0.4 to 4 Hertz with the aid of trimpot 156. This frequency is divided by two by Motorola 4013 "D" flip-flops 256. The complemented outputs of flip-flop 256 are software gated with the aid of a pair of Motorola 4001 NOR gates 258. The outputs of NOR gates 258 are then "NOR'd" with the output signals produced by EOG "left" and "right" push-buttons 160 and 162, thus enabling the push-buttons to override the "automatic" triggering of EOG lights 110 and 112. The "left" and "right" signals then each gate 2N3906 transistors 260 which, respectively, switch light emitting diode pairs 110/164 and 112/166.

Current signals produced by photo diode 108 in stimulator bowl 10 create a voltage potential across 10k ohm resistor 262. The resultant voltage is low pass filtered and amplified with the aid of an RCA 3140 integrated circuit 264 which is configured as a voltage follower. The resulting signal, which is representative of the background irradiance in stimulator bowl 10, is amplified by a National Semiconductor LM324 operational amplifier 266 and presented to channel 0 of analog to digital converter 198. The voltage potential obtained from voltage follower 264 is also used as the reference level for a second RCA 3140 integrated circuit 268 which integrates any potential above this level (i.e. any light pulses above the ambient light level) onto a 0.1 microfarad capacitor 270 when Motorola 4016 switch 272 is "on". Capacitor 270 is discharged by Motorola 4016 switch 274 whenever a pre-trigger pulse is software triggered via transistor 238. Switches 272 and 274 are each software driven with the aid of 2N3906 transistors 236 and 238.

The voltage signal representative of the background irradiance in stimulator bowl 10 is subtracted from the integrated flash radiant energy with the aid of National Semiconductor LM324 differential amplifier 276. The resultant signal, which is representative of the radiant energy in stimulator bowl 10, is amplified by a second National Semiconductor LM324 operational amplifier 278 and presented to a third National Semiconductor LM324 operational amplifier 280 which filters out any negative potentials which might harm analog to digital converter 198. The resultant signal is then presented to channel 5 of analog to digital converter 198 for further processing to derive therefrom further output signals representative of the radiometric or photometric characteristics of the radiant energy in stimulator bowl 10, such as radiance, irradiance, radiant flux, luminance, illuminance, luminous flux, etc. as may be desired. In particular, in the preferred embodiment, one such further output signal is a "second" output signal representative of the light flux at photo diode 108. The "second" output signal may be compared with a calibration signal (provided by the software from a look-up table) representative of the light flux expected from the flaslight source for a given aperture setting of light shutter 70, thus facilitating attenuation calibration of the light shutter as hereinbefore described.

Figure 3:
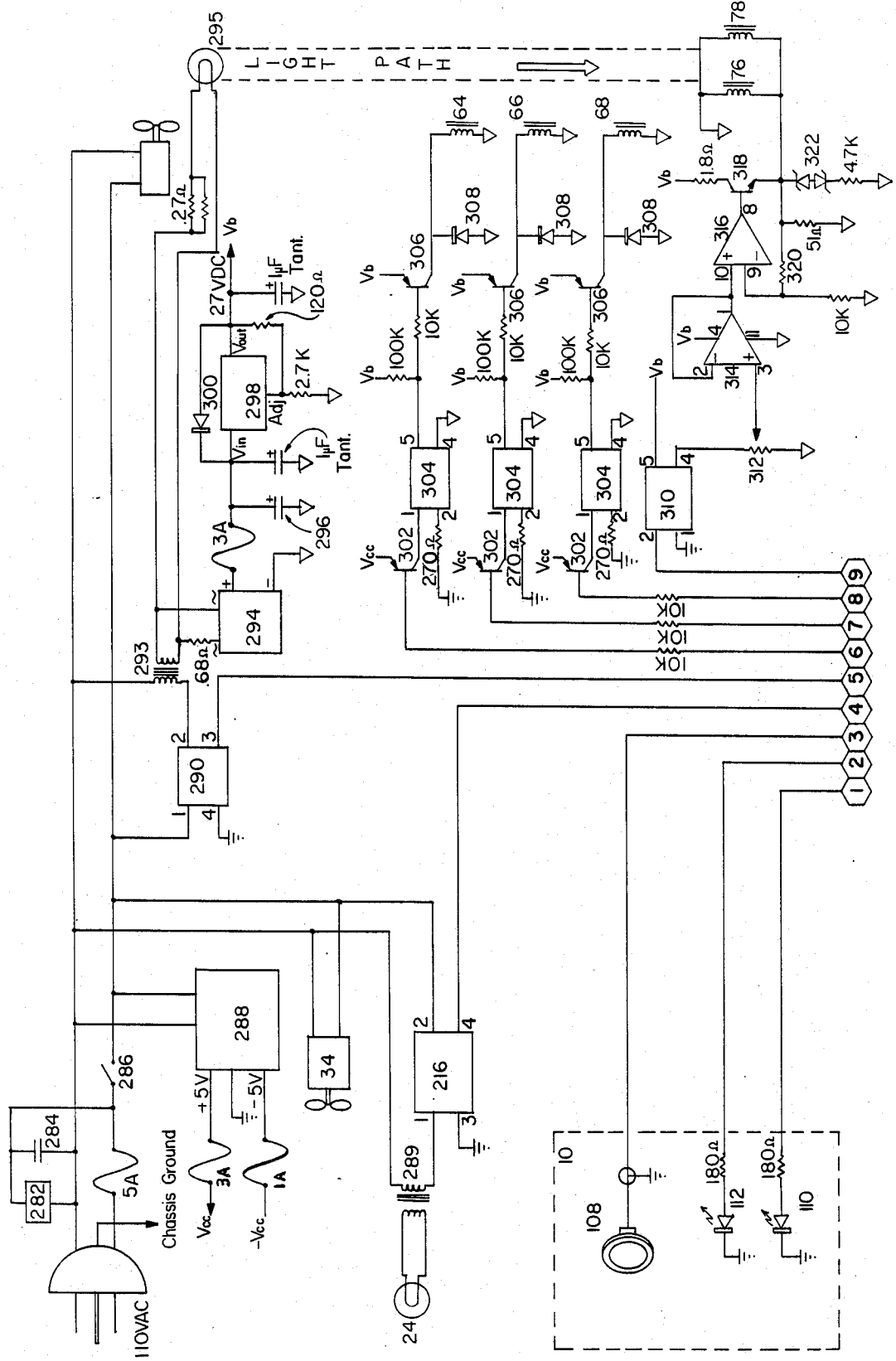
FIG. 3 is a block/schematic diagram of the power supply and optics control circuitry of the preferred embodiment.

With reference to FIG. 3, the 110-volt alternating current line voltage is filtered by a General Electric V130LA20A varistor 282 and a 0.1 microfarad capacitor 284. The line voltage is then switched by the main on/off switch 286 for presentation to the various power supplies.

A ±5 volt signal is obtained with a model HBB5-3 Power-One power supply 288. The power supply for background lightbulb 24 (which is a Philips FCS 24-volt, transformer 289 whose primary is switched by a Crydom D1202 relay 216 which is in turn software controlled by background light switch 114. Background light source cooling fan 34 is on whenever switch 286 is in the "on" position.

A Crydom D1210 solid-state relay 290 controlled by a software driven 2N3906 switching transistor 292 (FIG. 4) controls a second 25-volt transformer 293 which powers another Philips FCS 24-volt, 150-watt lightbulb 295 which serves as the light source in the flashlight section. A 200-volt, 8-amp bridge rectifier 294, a 75-volt, 4200 microfarad ripple filtering capacitor 296 and a National Semiconductor LM350 voltage regulator 298 are used to regulate the secondary output voltage of transformer 293 to 27 volts. A 1N4002 diode 300 is placed backwards across voltage regulator 298 to protect it from residual back currents after the power supply is switched off. The 27-volt supply is used to drive rotary solenoids 64, 66 and 68 and galvanometers 76 and 80.

Rotary solenoids 64, 66 and 68 are software controlled with the aid of 2N3906 switching transistors 302 which saturate Motorola 4N29 optical isolators 304. The switched output of optical isolators 304 is used to gate MJE2955 power transistors 306 which, in turn, switch on Ledex model A-35235-035 rotary solenoids 64, 66 or 68. 1N4004 diodes 308 suppress the reverse EMF of solenoids 64, 66 and 68.

The current output from digital to analog converter 202 directly drives another Motorola 4N29 optical isolator 310. The current regulated output of optical isolator 310 creates a voltage potential across 1k ohm trimpot 312 directly proportional to the output current digital to analog converter 202. Trimpot 312 controls the master gain of light shutter 70. The output from trimpot 312 is fed to a National Semiconductor LM324 operational amplifier 314 which is configured as a voltage follower. The output signal from voltage follower 314 is amplified by a second National Semiconductor LM324 operational amplifier 316. The amplified output signal biases Motorola MJE3055 power transistor 318 which regulates the drive current for galvanometers 76 and 78. A feedback loop through 10k ohm resistor 320 improves the step response of light shutter 70. Back-to-back 1N4736 zener diodes 322 suppress the reverse EMF of galvanometers 76 and 78. Galvanometers 76 and 78 are each M.F.E. model R4-155 galvanometers.

The values of electronic components not specifically described herein are shown in the drawings.

VIII. Software

Appendix "A" to this specification is a 45 page source code listing for a computer program developed for the preferred embodiment. The computer program is written in the "C" programming language. It is believed that the computer program listing, together with the many explanatory comments embedded therein, will enable those skilled in the art to understand the operation of the computer program.

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

APPENDIX A

```
/****************************************************************/
/*   DEFINE.ERG  *                                              */
/*****************                                              */
/*                                                              */
/*  This routine defines the three structures necessary for directly  */
/*      accessing specific parts of the memory, and all the defini-   */
/*      tions used globally by the program.                           */
/*                                                              */
/*                                                              */
/****************************************************************/

/* The following structures are used to trick the language into refer-  */
/*    ing to tables stored in specific spots in memory.                 */

/* The A-natural program 'hdrers.3' stores the display calibration      */
/*    table for the background light in the EPROM memory starting at   */
```

```
/*    location 44 (hex). This structure defines a reference to that      */
/*    table.                                                             */
struct
    begin
    unsigned short b_table[256];
    end;
#define t_back        (0x44->b_table)

/* The A-natural program 'hdrers.8' stores the display calibration       */
/*    table for the flash energy in the EPROM memory starting at         */
/*    location 245 (hex). This structure defines a reference to that     */
/*    table.                                                             */
struct
    begin
    unsigned short f_table[256];
    end;
#define t_flash       (0x245->f_table)

/* This structure defines a reference to the table in the EEPROM which   */
/*    calibrates the attenuation setting on the control panel to the     */
/*    appropriate shutter opening.                                       */
struct
    begin
    unsigned char c_table[64];
    end;
#define t_cal         (0x4000->c_table)

/* Input port definitions for the various analog to digital conversions  */
/*    that set the analog multiplexer and start the conversion           */
#define AD_BACK       0xE0    /* Background light (Irradiance) in the bowl */
#define AD_DOUBLE     0xE4    /* Trimpot adjustment for interval between    */
                              /*    double flashes                          */
#define AD_FLASH      0xE5    /* Flash energy in the bowl                   */
#define AD_GALVO      0xE3    /* Trimpot adjustment for length of flash     */
#define AD_L_EOG      0xEA    /* Left EOG signal                            */
#define AD_PEN        0xE6    /* Pen up or down from the signal averager    */
#define AD_TRIG       0xE2    /* Trimpot adjustment for pre-trigger interval*/
#define AD_R_EOG      0xE9    /* Right EOG signal                           */
#define AD_X          0xE7    /* X axis from the signal averager            */
define AD_Y          0xE8    /* Y axis from the signal averager            */ define COM1          0x80    /* Command register for the Intel 8155 chip   */
                              /*    that handles all the output ports except*/
                              /*    the digital display                     */
#define COM2          0xC0    /* Command register for the Intel 8155 chip   */
                              /*    that handles the output ports for the   */
                              /*    digital display                         */
#define DUD           0x00    /* Commonly used during an 'out' instruction  */
                              /*    when only the address and not the data  */
                              /*    is significant                          */
#define F_HIGH        0x01    /* Bit sequence to set the rst 6.5 interupt   */
                              /*    clock to the high frequency             */
#define F_LOW         0x02    /* Bit sequence to set the rst 6.5 interupt   */
                              /*    clock to the low frequency              */
#define F_OFF         0x03    /* Bit sequence to turn off the rst 6.5       */
                              /*    interupt clock                          */
#define IN1           0x40    /* First input port                           */
#define IN2           0x20    /* Second input port                          */
#define IN3           0x00    /* Third input port                           */
#define IN_ADC        0x60    /* Input port for the digitized analog signal */
#define L             1       /* Left eye data for use with EOG routines    */

/* The following definitions are used to mask in various bits that       */
/*    contain the desired information                                    */
#define M_CALIB       0x01    /* Status of the calibration back panel       */
                              /*    switch which should be used with input  */
                              /*    port IN3                                */
```

```
#define M_CEOG       0x10   /* Status of the EOG clock which should be      */
                            /*    used with input port IN3                  */
#define M_CHROM      0x70   /* Status of the chromatic filter select        */
                            /*    switch which should be used with input    */
                            /*    port IN1                                  */
#define M_DBACK      0x08   /* Status of the Background light switch        */
                            /*    which should be used with input port IN3  */
#define M_DEOG       0x02   /* Status of the EOG Auto/Manual switch which   */
                            /*    should be used with input port IN1        */
#define M_DISPLAY    0x80   /* Status of flash energy/irradiance switch,    */
                            /*    which should be used with input port IN1  */
#define M_DSELECT    0x07   /* Output of panel lamps for the messages       */
                            /*    'FLASH LENGTH', 'DOUBLE INTERVAL', and    */
                            /*    'PRE-FLASH INTERVAL', which should be     */
                            /*    used with output port OUT2                */
#define M_EMPTY      0x04   /* Status of serial port, which should be       */
                            /*    used with input port SER_STAT             */
#define M_EOC        0x40   /* Status of EOC of the analog to digital       */
                            /*    convertor, which should be used with      */
                            /*    input port IN3                            */
#define M_GALVO      0x40   /* Output of shutter status which should be     */
                            /*    used with output port OUT1                */
#define M_H_GALVO    0x80   /* Status of pin that can hold the shutter      */
                            /*    open which should be used with input      */
                            /*    port IN3                                  */
#define M_INTER      0x03   /* Mask used to blank out the two bits which    */
                            /*    enable the two interupt frequencies       */
#define M_LIGHT      0x04   /* Turn flash section light source on or off.   */
                            /*    Use with output port OUT1                 */
#define M_MODE       0x0C   /* Status of rate selection switch, which       */
                            /*    should be used with input port IN1        */
#define M_OUT_CAL    0x08   /* Turn 'out of calibration' light on or off.   */
                            /*    Use with output port OUT1                 */
#define M_READY      0x80   /* Status of the plotter input buffer which     */
                            /*    should be used with input port SER_DAT    */
#define M_REPEAT     0x01   /* Status of repeat switch, which should be     */
                            /*    used with input port IN1                  */
#define M_RST65      0x80   /* Output whether the program is in the         */
                            /*    interupt or not. Use with output port     */
                            /*    OUT1                                      */
#define M_SBACK      0x02   /* Turn background light on or off. Use with    */
                            /*    output port OUT3                          */
#define M_SELECT     0x02   /* Status of calibration select push-button     */
                            /*    which should be used with input port IN3  */
#define M_SEOG       0x10   /* Turn EOG oscillator on or off. Use with      */
                            /*    output port OUT1                          */
#define M_SHOLD      0x01   /* Output sample and hold pulse. Use with       */
                            /*    output port OUT3                          */
#define M_SINGLE     0x04   /* Detects if single flash sequence has been    */
                            /*    called for. Use with input port IN3       */
#define M_TRIG       0x20   /* Output the pre-trigger pulse when used       */
                            /*    with output port OUT1                     */ define N_OFF        0xFF   /* Turn off a port using negative logic         */
define OUT1         0x81   /* Output port                                  */
#define OUT2         0x83   /* Output port                                  */
#define OUT3         0xC3   /* Output port                                  */
#define OUT_D1       0xC1   /* Output port for 'one' and 'tens' digits      */
                            /*    display                                   */
#define OUT_D2       0xC2   /* Output port for 'hundreds' digit display     */
                            /*    and the four decimal points               */
#define OUT_DAC      0x82   /* Output port to the digital to analog con-    */
                            /*    verter that controls the shutter          */
#define OVERFLOW     0x7FF  /* Can be used to indicate an over-flow con-    */
                            /*    dition to the display routine             */
```

```c
#define P_OFF       0x00    /* Turn off a port using positive logic        */
#define R           0       /* Right eye data to be used with EOG          */
                            /*   routines                                  */
#define RECALL      0xA1    /* Strobe port to recall contents of EEPROM    */
                            /*   onto on-chip RAM                          */
#define SER_DATA    0xA3    /* Port for input and output of data to the    */
                            /*   serial communications chip, INTEL 8251A   */
#define SER_STAT    0xAB    /* Port for input and output of status and     */
                            /*   command words to the INTEL 8251A          */
#define ST_CON      0xA2    /* Strobe port to start analog to digital      */
                            /*   conversion                                */
#define STA_TI      0xCF    /* Command word to set the ports and start     */
                            /*   the timer on the 8155 chip                */
#define STOP_TI     0x4F    /* Command word to set the ports and stop the  */
                            /*   timer on the 8155 chip                    */
#define STORE       0xA0    /* Strobe port to store contents of shadow     */
                            /*   RAM into the EEPROM                       */

/****************************************************************************/
/* GLOBAL.ERG  *                                                            */
/***************                                                            */
/*                                                                          */
/*   This routine does all the global definitions.                          */
/*                                                                          */
/****************************************************************************/ unsigned char bcd[4]=0;         /* Array used in converting the Binary      */
                                /*   Coded Decimal of the attenuation       */
                                /*   select switch into binary              */
unsigned char eos_a[2][31]=0;   /* EOG amplitude data for both eyes and     */
                                /*   every minute                           */
unsigned char expected[41]=0;   /* Table which defined in the routine       */
                                /*   init(), contains the binary            */
                                /*   values for the flash at all            */
                                /*   possible attenuation settings          */ unsigned short atten=0;         /* Attenuation switch setting               */
unsigned short b_back=0;        /* Binary value of background irradiance    */
unsigned short b_flash=0;       /* Binary value of last flash energy        */
unsigned short back=0;          /* Calibrated value of background light     */
unsigned short c_out1=0;        /* Current value of output port OUT1        */
unsigned short c_out2=0;        /* Current value of output port OUT2        */
unsigned short c_out3=0;        /* Current value of output port OUT3        */
unsigned short change=0;        /* Positive logic flag used to indicate     */
                                /*   that the EEPROM table should be        */
                                /*   re-stored                              */
unsigned short crash=0;         /* Positive logic flag that indicates to an */
                                /*   interupt routine that an analog to     */
                                /*   digital conversion was in progress     */
unsigned short d_hund=0;        /* BCD value of the hundreds display digit  */
unsigned short d_one=0;         /* BCD value of the ones display digit      */
unsigned short d_ten=0;         /* BCD value of the tens display digit      */
unsigned short doubl=0;         /* Positive logic flag that indicates if    */
                                /*   double rate is called for              */
unsigned short eos_fin=0;       /* Positive logic flag that indicates when  */
                                /*   the EOG test sequence has been com-    */
                                /*   pleted                                 */
unsigned short error=0;         /* Counter of flash calibration errors      */
unsigned short f_expect=0;      /* Expected value of flash that has been    */
                                /*   corrected for background light and     */
                                /*   shutter opening length                 */
unsigned short flash=0;         /* Calibrated value of the last flash       */
unsigned short salvo=0;         /* Binary calibrated value of the shutter   */
                                /*   opening to be sent to the analog to    */
                                /*   digital converter                      */
unsigned short hex=0;           /* Positive logic flag that indicates if    */
```

```
unsigned short high=0;      /* the routine display() should leave the */
                            /* data it receives in hexadecimal format */
                            /* Positive logic flag which indicates if  */
                            /*    the rate is set at high              */
unsigned short in_calib=0;  /* Positive logic flag which indicates that*/
                            /*    the device is in a calibration       */
                            /*    sequence: if set to 1 its the cali-  */
                            /*    brating one of the three trimpots, if*/
                            /*    set to 2 its calibrating the attenua-*/
                            /*    tion switch                          */
unsigned short l_err=0;     /* Coded indication of errors during an EOG*/
                            /*    test for the left eye                */
unsigned short light_on=0;  /* Positive logic flag that indicates the  */
                            /*    status of the flash light source     */
unsigned short loop=0;      /* Counter of loops through the main pro-  */
                            /*    gram. Its used to slow down the rate */
                            /*    of data output to the digital display*/
unsigned short low=0;       /* Positive logic flag which indicates if  */
                            /*    the rate is set to low or not        */
unsigned short max_eos[2]=0;/* Maximum amplitude for both eyes during  */
                            /*    the EOG test                         */
unsigned short min_eos[2]=0;/* Minimum amplitude for both eyes during  */
                            /*    the EOG test                         */
unsigned short mode=0;      /* Temporary bit pattern readout of the    */
                            /*    rate switch                          */
unsigned short range=0;     /* Allowable range of error for the flash  */
                            /*    error detection software             */
unsigned short repeat=0;    /* Positive logic flag which indicates if  */
                            /*    the mode switch is in the repeat po- */
                            /*    sition                               */
unsigned short r_err=0;     /* Coded indication of errors in the signal*/
                            /*    from the right eye during the EOG test*/
unsigned short select=0;    /* Rotating bit which indicates which of   */
                            /*    the three trimpots is being cali-    */
                            /*    brated                               */
unsigned short single=0;    /* If equal to 1 this means a single flash */
                            /*    sequence is desired. This variable   */
                            /*    is set to 2 when the sequence is per-*/
                            /*    formed and reset to 0 when the single*/
                            /*    input has gone low                   */
unsigned short t_double=0;  /* Time delay between double flashes       */
unsigned short t_salvo=0;   /* Time delay while shutter is open        */
unsigned short t_trig=0;    /* Time delay between start of pre-trigger */
                            /*    pulse and the flash                  */
unsigned short thumb=0;     /* Bit readings of the thumbwheel attenua- */
                            /*    tion switch                          */
unsigned short time=0;      /* Counter to determine when the flash     */
                            /*    source should be turned off          */ short l_range=0;            /* Lower limit of expected value of flash  */
unsigned short minutes=0;   /* Time that has passed during an EOG test */

/***********************************************************************/
/* MAIN.ERG      *                                                      */
/*****************                                                      */
/*                                                                      */
/* This routine is called by the A-Natural program 'hdrerg.8' and       */
/*     in turn calls all the 'C' language routines to operate the       */
/*     stimulator. It first initializes all appropriate variables       */
/*     by calling init() and then enters the infinate loop of the       */
/*     main program. Here the calibration switch is checked and         */
/*     if on, calpot() is called to calibrate the three trimpots for    */
/*     flash length, double interval, and pre-trigger interval.         */
/*     Then calatt() is called, which allows the operator to manually   */
/*     change the calibration of the attenuation switch. Next,          */
/*     smode() is called which reads all the front panel switches and   */
/*     sets the appropriate variables to reflect its status.            */
```

```
/*      If a single flash sequence is called for then rst65() is          */
/*      called. If the 'select' pushbutton on the back panel is pres-     */
/*      sed then the automatic attenuation calibration routine,           */
/*      autcal() is called. A check is made to see if the penlift line    */
/*      and if so plot() is called to plot the ERG traces. A reading      */
/*      of background irradiance is then taken, and the background        */
/*      irradiance or the flash energy is displayed, depending on the     */
/*      setting of the front panel switch. Lastly if the EOG switch is    */
/*      on and a test has not been completed, eos() is called.            */
/*                                                                        */
/*      THIS ROUTINE CALLS:                                               */
/*              init()              smode()                               */
/*              calpot()            autcal()                              */
/*              calatt()            rst65()                               */
/*              display()           delay()                               */
/*              adc()               plot()                                */
/*              eos()                                                     */
/*                                                                        */
/*      GLOBALS:                                                          */
/*              in_calib            loop                                  */
/*              single              crash                                 */
/*              b_back              flash                                 */
/*              back                t_back                                */
/*              eos_fin                                                   */
/*                                                                        */
/*      AUTOMATIC LOCALS:                                                 */
/*              none used                                                 */
/*                                                                        */
/*      ARGUMENTS:                                                        */
/*              none used                                                 */
/*                                                                        */
/*      CONSTANTS:                                                        */
/*              IN3                 M_CALIB                               */
/*              M_SELECT            AD_BACK                               */
/*              IN1                 M_DISPLAY                             */
/*              AD_PEN              M_DEOG                                */
/*                                                                        */
/**************************************************************************/ main()
    begin
    init();          /* Initialize globals   */
    for(;;)
        begin
        calatt();                /* Manual calibration of attenuation switch   */
        while (!(in (IN3) & M_CALIB))    /* Calibration switch is on           */
            begin
            in_calib = 1;
            smode ();            /* Read front panel    */ if (single == 1)
                rst65 ();

calpot();            /* Calibrate one of the three trimpots    */ delay (1000);        /* Slow down the output to the display    */
            in_calib = 0;
            end
        smode ();    /* Read front panel   */ if (single == 1)
            rst65 ();
        if (!(in (IN3) & M_SELECT))      /* If 'select' pushbutton is          */
            autcal();                    /*    pressed then perform            */
                                         /*    automatic calibration           */
        if (adc(AD_PEN) < 100)           /* If the penlift input goes low      */
```

```
              if (adc(AD_PEN) < 100)      /*   then a plot of the ERG    */
                  if (adc(AD_PEN) < 100)  /*   traces is expected        */
                      plot();

crash = 1;
        b_back = adc(AD_BACK);          /* Get readings of background    */
        back = t_back[b_back];          /*   irradiance                  */
        crash = 0;

loop += 1;
        if (loop > 100)
            begin
            loop = 0;
            if (in (IN1) & M_DISPLAY)   /* Measurement of background     */
                display (back);         /*   irradiance to be displayed  */
                else display (flash);   /* Flash energy to be displayed  */
            end if (!(in(IN1) & M_DEOG) && !eos_fin)
            then eos();
            else eos_fin = 0;
        end
    end /*************************************************************************/
/*  ADC.ERG    *                                                         */
/***************                                                         */
/*                                                                       */
/*  This routine return the value of an analog to digital conversion     */
/*      on the analog port given as an argument.                         */
/*                                                                       */
/*      THIS ROUTINE CALLS:                                              */
/*          delay()                                                      */
/*                                                                       */
/*      GLOBALS:                                                         */
/*          none used                                                    */
/*                                                                       */
/*      AUTOMATIC LOCALS:                                                */
/*          none used                                                    */
/*                                                                       */
/*      ARGUMENTS:                                                       */
/*          unsigned short port - analog input port                      */
/*                                                                       */
/*      CONSTANTS:                                                       */
/*          DUD                     IN3                                  */
/*          M_EOC                   IN_ADC                               */
/*                                                                       */
/*************************************************************************/ adc(port)
unsigned short port;
    begin
    out (port, DUD);    /* Set analog multiplexer and start conversion   */
    delay (3);          /* Wait awhile to make sure EOC has gone high    */
    while (in (IN3) & M_EOC)   /* Data ready when EOC goes low           */
        ;
    return (in (IN_ADC));      /* Return value of conversion             */
    end /*************************************************************************/
/*  ADCPOT.ERG  *                                                        */
/****************                                                        */
/*                                                                       */
/*  This routine returns the scaled and offset value of the analog       */
/*      channel given by the argument 'port'. It is used to read the     */
/*      values of one of the three calibration trimpots, 'flash          */
/*      length', 'double interval' and 'pre-trigger interval'. The       */
```

```
/*      potential of the trimpot is converted to an 8 bit digital          */
/*      number, scaled accordins to the argument 'r_shift' and added        */
/*      to the offset indicated by the argument 'base'. This produces      */
/*      a number suitable for use with the software time delay,            */
/*      delay(), since there is an internal multiplication of 160.          */
/*                                                                          */
/*      THIS ROUTINE CALLS:                                                 */
/*          adc()                                                           */
/*                                                                          */
/*      GLOBALS:                                                            */
/*          none used                                                       */
/*                                                                          */
/*      AUTOMATIC LOCALS:                                                   */
/*          unsigned short temp - temporary value between calculations     */
/*                                                                          */
/*      ARGUMENTS:                                                          */
/*          unsigned short port - analog input port                         */
/*          unsigned short r_shift - binary places that the ADC value      */
/*                                   is scaled by                           */
/*          unsigned short base - offset that the final scaled value       */
/*                                is shifted by                             */
/*                                                                          */
/*                                                                          */
/*      CONSTANTS:                                                          */
/*          none used                                                       */
/*                                                                          */
/**************************************************************************/ adcpot (port, r_shift, base)
unsigned short port, r_shift, base;

begin
    unsigned short temp;
    temp = adc (port) >> r_shift;
    return ((((temp << 1) + (temp << 3)) << 4) + base);
    end /**************************************************************************/
/*   AMPLIT.ERG   *                                                         */
/*****************                                                          */
/*                                                                          */
/*   This routine determines the amplitude of the right and left EOG       */
/*      inputs for one switch of the lights. It is assumed that the         */
/*      polarity of the EOG signal is such that the right eye makes         */
/*      a positive step and the left eye makes a negative step. For         */
/*      the first 80 milliseconds a baseline is established. If the         */
/*      deviation from this baseline is too large, then for the right       */
/*      eye r_err is set to 1, and for the left eye l_err is set to 1.     */
/*      The routine then searches for the peak signal over the next         */
/*      750 milliseconds and calls the difference the amplitude. The        */
/*      variables r_err for the right eye and l_err for the left eye,       */
/*      are set to 2 if the peak signal goes off scale.                     */
/*                                                                          */
/*      THIS ROUTINE CALLS:                                                 */
/*          adc()              delay()                                      */
/*                                                                          */
/*      GLOBALS:                                                            */
/*          r_err              l_err                                        */
/*                                                                          */
/*      AUTOMATIC LOCALS:    (preceeding 'r' is for right eye              */
/*                            and preceeding 'l' is for left eye)          */
/*          unsigned short step - incrementer for loops                     */
/*          unsigned short r_wave[16], l_wave[16] - Table which holds      */
/*                            the baseline values to be averaged            */
/*          unsigned short r_total, l_total - running totals of values     */
/*                            to be averaged                                */
```

```
/*          unsigned short r_baseline, l_baseline - baseline of EOG     */
/*                          signals before the light switch             */
/*          unsigned short r_deviation, l_deviation - deviation in the  */
/*                          baseline signal                             */
/*          unsigned short r_max, l_max - peak amplitudes               */
/*          unsigned short temp - temporary storage for variables after */
/*                          an analog to digital conversion             */
/*                                                                      */
/*      ARGUMENTS:                                                      */
/*          unsigned short *r_amp, *l_amp - EOG amplitudes to be        */
/*                          returned to the calling routine             */
/*                                                                      */
/*      CONSTANTS:                                                      */
/*          AD_R_EOG            AD_L_EOG                                */
/*                                                                      */
/**********************************************************************/ amplit (r_amp, l_amp)
unsigned short *r_amp, *l_amp;

begin
    unsigned short step;
    unsigned short r_wave[16], l_wave[16];
    unsigned short r_total, l_total, r_baseline, l_baseline;
    unsigned short r_deviation, l_deviation;
    unsigned short r_max, l_max, temp;
    r_total = l_total = 0;

for (step=0; step<16; step++)
        begin
        r_wave[step] = adc (AD_R_EOG);
        l_wave[step] = adc (AD_L_EOG);
        delay (80);
        r_total += r_wave[step];    /* Get running total of baseline    */
        l_total += l_wave[step];    /*    values                        */
        end r_baseline = r_total >> 4;  /* Average to find the baseline         */
    l_baseline = l_total >> 4;
    r_total = l_total = 0;

for (step=0; step<16; step++)
        begin   /* Find the total of the absolute deviations            */
        if (r_wave[step] > r_baseline)
            then r_total += (r_wave[step] - r_baseline);
            else r_total += (r_baseline - r_wave[step]);
        if (l_wave[step] > l_baseline)
            then l_total += (l_wave[step] - l_baseline);
            else l_total += (l_baseline - l_wave[step]);
        end r_deviation = r_total >> 4;     /* Find the average deviation from  */
    l_deviation = l_total >> 4;     /*    the baseline value            */
    if (r_deviation > 50)           /* Set error flags if the average   */
        then r_err = 1;             /*    deviation is too large        */
        else r_err = 0;
    if (l_deviation > 50)
        then l_err = 1;
        else l_err = 0;

r_max = 0;
    l_max = 255;
    for (step=0; step<150; step++)
        begin                           /* Find the positive peak for   */
        temp = adc (AD_R_EOG);          /*    the right eye and the     */
        if (temp == 255)                /*    negative peak for the     */
            r_err = 2;                  /*    left eye                  */
```

```
            if (temp > r_max)
                r_max = temp;
            temp = adc (AD_L_EOG);
            if (temp == 0)
                l_err = 2;
            if (temp < l_max)
                l_max = temp;
            delay (80);
            end if (r_err == 0)                         /* Return amplitude values   */
        then *r_amp = r_max - r_baseline;   /*   only if no errors have  */
        else *r_amp = 0;                    /*   occurred                */
    if (l_err == 0)
        then *l_amp = l_baseline - l_max;
        else *l_amp = 0;
    end
```

```
/**************************************************************************/
/* AUTCAL.ERG  *                                                          */
/***************                                                          */
/*                                                                        */
/* This routine performs the automatic calibration of c_table[],          */
/*     which is the look-up table to match the control panel atten-       */
/*     uation setting to the appropriate shutter opening.  It waits       */
/*     until the background irradiance is set to zero, sets the flash     */
/*     length to 20 milliseconds, and then cycles through all the         */
/*     attenuation settings (0 to 40dB), which are shown on the           */
/*     display as they are being processed.  If the obtained flash        */
/*     energy falls out of range of the expected flash energy, as         */
/*     indicated by the routine calfsh(), three times in a row, then      */
/*     a binary search is made of the possible shutter openings until     */
/*     a value is found that falls within the expected range, or until    */
/*     the upper and lower bounds of the search meet.  This routine       */
/*     is aborted if the calibration button, which originally caused      */
/*     this routine to be called, in released.                            */
/*                                                                        */
/*     THIS ROUTINE CALLS:                                                */
/*         adc()               calfsh()                                   */
/*         display()           delay()                                    */
/*         setbit()            resetbit()                                 */
/*                                                                        */
/*     GLOBALS:                                                           */
/*         expected[]          in_calib                                   */
/*         b_back              c_out1                                     */
/*         b_flash             t_salvo                                    */
/*         atten               salvo                                      */
/*         t_cal[]                                                        */
/*                                                                        */
/*     AUTOMATIC LOCALS:                                                  */
/*         unsigned short low  - lower bound for binary search            */
/*         unsigned short high - upper bound for binary search            */
/*         unsigned short temp_salvo - temporary storage for the          */
/*                                     original value of 'salvo'          */
/*                                                                        */
/*     ARGUMENTS:                                                         */
/*         none used                                                      */
/*                                                                        */
/*     CONSTANTS:                                                         */
/*         AD_BACK             DUD                                        */
/*         IN3                 M_SELECT                                   */
/*         M_OUT_CAL           OUT1                                       */
/*         STORE                                                          */
/*                                                                        */
/**************************************************************************/
```

```
autcal()
    begin
    unsigned short low, high, temp_salvo;
    in_calib = 2;               /* Indicate calibration of attenuation     */
                                /*   switch is in progress                 */
    b_back = adc (AD_BACK);
    while (b_back > 0)          /* Wait until the background irradiance    */
        begin                   /*   becomes zero                          */
        display (DUD);
        b_back = adc (AD_BACK);
        end
    temp_salvo = t_salvo;       /* Save original value of flash length     */
    t_salvo = (20 << 4) - 1;    /* Set flash length to 20 milliseconds     */
    atten = 0;

while ((atten<41) && !(in(IN3) & M_SELECT))
        begin
        display (atten);        /* Display attenuation setting being       */
        salvo = t_cal[atten];   /*   calibrated                            */
        if (!calfsh())          /* Give the flash three chances to         */
            begin               /*   produce the expected flash            */
            delay (16000);      /*   energy                                */
            if (!calfsh())
                begin
                delay (16000);
                if (!calfsh())
                    begin
                    delay (16000);
                    setbit (M_OUT_CAL, &c_out1, OUT1);   /* Turn on OUT    */
                                                         /* OF CALIBRATION light */
                    if (b_flash < expected[atten])
                        then    /* Flash is less than expected so set      */
                            begin    /*   bounds to lower portion          */
                            low = t_cal[atten];
                            high = 255;
                            end
                        else    /* Flash is greater than expected so set   */
                            begin    /*   bounds to upper portion          */
                            low = 140;
                            high = t_cal[atten];
                            end
                    salvo = (low + high) >> 1;    /* Set shutter opening   */
                                                  /* to middle of bounds   */
                    while ((!calfsh()) && !(in(IN3)&M_SELECT) && (low<high))
                        begin    /* Perform binary search                  */
                        if (b_flash < expected[atten])
                            low = salvo;
                            else high = salvo;
                        salvo = (low + high) >> 1;
                        delay (16000);
                        end
                    t_cal[atten] = salvo;    /* Permanently store new      */
                    out (STORE, DUD);        /*   calibrated value         */
                    delay (200);
                    resetbit (M_OUT_CAL, &c_out1, OUT1);   /* Turn off     */
                    end                                    /* OUT OF CALIBRATION light */
                end
            end
        ++atten;    /* Try next attenuation setting     */
        end
    t_salvo = temp_salvo;    /* Restore original value of flash length     */
    in_calib = 0;
    end /******************************************************************/
/*    CALATT.ERG    *                                              */
```

```
/****************                                                           */
/*                                                                          */
/* This routine allows the operator to manually change the calibration      */
/*     of the attenuation switch. It is entered or aborted by               */
/*     toggling the calibration switch, an action which would not nor-      */
/*     mally be done on the control panel. For any attenuation set-         */
/*     ting, the display will show the current DAC setting from the         */
/*     table t_cal[]. This value can be changed by pushing the              */
/*     'select calibration' button. If the button is held, the              */
/*     display will count slowly for the first four counts and rapidly      */
/*     thereafter. The direction of count is determined by the              */
/*     'calibration' toggle switch.                                         */
/*                                                                          */
/*     THIS ROUTINE CALLS:                                                  */
/*          delay()             setbit()                                    */
/*          smode()             rst65()                                     */
/*          display()           resetbit()                                  */
/*                                                                          */
/*     GLOBALS:                                                             */
/*          in_calib            change                                      */
/*          c_out1              single                                      */
/*          salvo               flash                                       */
/*          t_cal[]              atten                                      */
/*                                                                          */
/*     AUTOMATIC LOCALS:                                                    */
/*          unsigned short count - used to keep track of the number         */
/*                                 of counts that the 'select cali-         */
/*                                 bration' is pressed for                  */
/*                                                                          */
/*     ARGUMENTS:                                                           */
/*          none used                                                       */
/*                                                                          */
/*     CONSTANTS:                                                           */
/*          M_OUT_CAL           OUT1                                        */
/*          M_DISPLAY           IN3                                         */
/*          M_SELECT            M_CALIB                                     */
/*          STORE               DUD                                         */
/*                                                                          */
/****************************************************************************/ calatt()
    begin
    unsigned short count;
    if (!(in (IN3) & M_CALIB))      /* Calibration switch must be toggled   */
        begin                        /*    at about .5 hz to enter the inner */
        delay (3200);                /*    loop                              */ if (in (IN3) & M_CALIB)
            begin
            delay (3200);

if (!(in (IN3) & M_CALIB))
                begin
                in_calib = 2;    /* Set flag that calibration of atten-     */
                change = 0;      /*    uation switch is in progress         */ while (in_calib)
                    begin
                    setbit (M_OUT_CAL, &c_out1, OUT1);  /* Turn on OUT      */
                                                         /* OF CALIBRATION light */
                    smode ();        /* Read control panel                  */ if (single == 1)    /* Perform single flash if          */
                        rst65 ();       /*    called for                    */
```

```
                    ++in_calib;            /* Set up short timer that will */
                                           /*   not allow the operator to  */
                                           /*-  immediately toggle out of  */
                    if (in_calib > 1000)   /*    the calibration mode      */
                        in_calib = 1000;

if (in (IN1) & M_DISPLAY)
                        display (salvo);
                        else display (flash); /* Display flash energy     */
                                              /* if flash energy switch is up */
                    count = 0;

while (((!(in(IN3)&M_SELECT))&&(in(IN1)&M_DISPLAY))
                        begin if (!(in (IN3) & M_CALIB))
                                begin
                                if (t_cal[atten] != 255)
                                    ++t_cal[atten];   /* Increment cal- */
                                end                   /* ibration setting */
                            else
                                if (t_cal[atten] != 0)
                                    --t_cal[atten];   /* Decrement cal- */
                                                      /* igration setting */
                        display (t_cal[atten]);
                        ++count;
                        change = 1;   /* Indicate that the EEPROM table */
                                      /*   has been changed and should  */
                                      /*   be restored                  */
                        if (count < 5)
                            delay (8000);   /* Slow count               */
                            else delay (1600); /* Fast count            */ end if ((!(in (IN3) & M_CALIB)) && (in_calib >= 1000))
                        begin               /* Test for cal. switch being */
                        delay (3200);       /*    toggled to abort this   */
                                            /*    routine                 */
                        if (in (IN3) & M_CALIB)
                            begin
                            in_calib = 0;
                            resetbit (M_OUT_CAL, &c_out1, OUT1);

if (change)     /* Restore table from shadow */
                                begin       /*    RAM into the EEPROM    */
                                out (STORE, DUD);
                                delay (200); /* Wait for end of store   */
                                end end
                        end
                    end
                end
            end
        end
    end /**********************************************************************/
/*   CALFSH.ERG   *                                                   */
/*****************                                                    */
/*                                                                    */
/*   This routine performs one flash, measures the received flash     */
/*      energy, compares it to the expected value of the flash        */
/*      plus or minus a small range and returns 1 if the flash is     */
/*      in calibration or 0 if the flash is out of calibration.       */
/*                                                                    */
```

```
/*      THIS ROUTINE CALLS:                                             */
/*          setbit()              delay()                               */
/*          resetbit()            open_salvo()                          */
/*          adc()                                                       */
/*                                                                      */
/*      GLOBALS:                                                        */
/*          c_out1                t_tris                                */
/*          b_flash               range                                 */
/*          expected[]            atten                                 */
/*          l_range                                                     */
/*                                                                      */
/*      AUTOMATIC LOCALS:                                               */
/*          none used                                                   */
/*                                                                      */
/*      ARGUMENTS:                                                      */
/*          none used                                                   */
/*                                                                      */
/*      CONSTANTS:                                                      */
/*          M_TRIG                OUT1                                  */
/*          AD_FLASH                                                    */
/*                                                                      */
/************************************************************************/ calfsh()
    begin
    setbit (M_TRIG, &c_out1, OUT1);    /* Send out pre-trigger pulse to  */
    delay (t_tris);                    /*    kill the charge stored on   */
    resetbit (M_TRIG, &c_out1, OUT1);  /*    the integrating capacitor   */
    open_salvo ();
    b_flash = adc (AD_FLASH);
    range = (expected[atten] / 10) + 4;  /* Determine allowable range of */
                                         /*    error                     */
    l_range = expected[atten] - range;   /* Make sure lower bound is not */
    if (l_range < 0) l_range = 0;        /*    negative                  */
    if ((b_flash < expected[atten] + range) && (b_flash >= l_range))
        return (1);              /* in calibration */
        else return (0);         /* out of calibration */
    end /************************************************************************/
/* CALPOT.ERG  *                                                         */
/***************                                                         */
/*                                                                       */
/* This routine allows the operator to select and change the adjust-     */
/*     ment of any one of the three trimpots, 'flash length', 'double    */
/*     interval', and 'pre-trigger length'. The name of the trimpot      */
/*     that is undergoing calibration is lit on the display and the      */
/*     value of that time adjustment in milliseconds is shown on the     */
/*     display. The different trimpots are selected by pressing the      */
/*     'select calibration' pushbutton.                                  */
/*                                                                       */
/*      THIS ROUTINE CALLS:                                              */
/*          adcpot()              display()                              */
/*                                                                       */
/*      GLOBALS:                                                         */
/*          select                t_tris                                 */
/*          flash                 t_salvo                                */
/*          t_double                                                     */
/*                                                                       */
/*      AUTOMATIC LOCALS:                                                */
/*          none used                                                    */
/*                                                                       */
/*      ARGUMENTS:                                                       */
/*          none used                                                    */
/*                                                                       */
/*      CONSTANTS:                                                       */
/*          AD_TRIG               AD_GALVO                               */
```

```
/*          AD_DOUBLE           IN1                                           */
/*          M_DISPLAY           IN3                                           */
/*          M_SELECT                                                          */
/*                                                                            */
/******************************************************************************/ calpot()
    begin
    switch (select)
        begin
        case 4:
            t_trig = adcpot (AD_TRIG, 5, 157); /* Set pre-trigger time */
            if (in (IN1) & M_DISPLAY)          /*     interval          */
                display ((t_trig >> 4) + 1);
                else display (flash);
            break;
        case 1:
            t_galvo = adcpot (AD_GALVO, 3, 157); /* Set length of flash */
            if (in (IN1) & M_DISPLAY)
                display ((t_galvo >> 4) + 1);
                else display (flash);
            break;
        case 2:
            t_double = adcpot (AD_DOUBLE, 2, 1597); /* Set time inter- */
            if (in (IN1) & M_DISPLAY)               /*    val between  */
                display ((t_double >> 4) + 1);      /*    double flashes */
                else display (flash);
            break;
        end if (!(in (IN3) & M_SELECT))     /* If 'select calibration' button is */
        begin                       /*    pressed then change selection  */
        select <<= 1;               /*    to the next trimpot            */
        if (select > 4)
            select = 1;
        while (!(in (IN3) & M_SELECT))  /* Make sure button is released */
            ;                           /*    before continuing         */
        end
    end /******************************************************************************/
/* CONDEN.ERG   *                                                             */
/****************                                                             */
/*                                                                            */
/* This routine will plot the condensed EOG amplitudes for the right          */
/*      and left eyes, with a written indication of both light rise           */
/*      ratios.  The output medium is an HP 7470A Graphics plotter            */
/*      via an RS232 interface.  The plotter commands are the HP              */
/*      Graphics Language mnemonics.                                          */
/*                                                                            */
/*      THIS ROUTINE CALLS:                                                   */
/*          serial()            move()                                        */
/*          fractn()                                                          */
/*                                                                            */
/*      GLOBALS:                                                              */
/*          eqs_a[2][31]        max_eos[2]                                    */
/*          min_eos[2]                                                        */
/*                                                                            */
/*      AUTOMATIC LOCALS:                                                     */
/*          unsigned short step - variable for stepping positions             */
/*                                across the graph                            */
/*          unsigned short minute - time value to be plotted                  */
/*                                                                            */
/*      ARGUMENTS:                                                            */
/*          none used                                                         */
/*                                                                            */
```

```
/*      CONSTANTS:                                                          */
/*          none used                                                       */
/*                                                                          */
/****************************************************************************/ conden()
    begin
    unsigned short step, minute;
    serial("IN");           /* Initialize plotter    */
    serial("\33\56\100");           /* Set handshaking to pin 20    */
    serial("CS0;SS;DT ;SP1;SC0,400,0,320");     /* Set X range to 400  */
    move (30, eos_a[R][0]+20);                  /*   and Y range to 320 */
    serial("PD");
    step = 40;
    for (minute=1; minute<=30; minute++)
        begin                   /* Plot right eye amplitudes     */
        if (eos_a[R][minute] > 0) move (step, eos_a[R][minute]+20);
        step += 10;
        end
    serial("PU;PA335,200;LBRight LBRatio LB= CP");  /* Print right light */
    fractn (max_eos[R], min_eos[R]);                /* rise ratio on the */
    serial("LT2,5;PA180,20;PD;PA180,270;PU;LT");    /* side of the graph */
    serial("PA78,260;LBDARK LBADAPTED PA225,260;LBLIGHT LBADAPTED SP2");
    move (30, eos_a[L][0]+20);
    serial("PD");
    step = 40;
    for (minute=1; minute<=30; minute++)
        begin                   /* Plot left  eye amplitudes     */
        if (eos_a[L][minute] > 0) move (step, eos_a[L][minute]+20);
        step += 10;
        end
    serial("PU;PA335,150;LBLeft LBRatio LB= CP");   /* Print left light */
    fractn (max_eos[L], min_eos[L]);                /* rise ratio on the */
    serial("PA330,20PD30,20,30,270PU;TL1.5,1.5");   /* side of the graph */
    for (step=270; step>20; step-=50)
        begin                   /* Put in Y scale tick marks         */
        move (30, step);
        serial("YT");
        end
    for (step=40; step<340; step+=10)
        begin                   /* Put in X scale tick marks         */
        move (step, 20);
        serial("XT");
        end                     /* Label scales and title the graph  */
    serial("PA326,10;LB30 PA226,10;LB20 PA126,10;LB10 PA28.5,10;LB0 ");
    serial("PA20,17.6;LB0 PA10,267.6;LB250 ");
    serial("PA0,145;LBuV PA163,0;LBMinutes ");
    serial("SI0.7,1.0;PA85,300;LBEOG LBAMPLITUDES SP0;");
    end /****************************************************************************/
/* DELAY.ERG   *                                                            */
/***************                                                            */
/*                                                                          */
/*  This routine provides a software delay of 62.5 microseconds per         */
/*      loop, or 1 millisecond for 16 loops.                                */
/*                                                                          */
/*      THIS ROUTINE CALLS:                                                 */
/*          nothing                                                         */
/*                                                                          */
/*      GLOBALS:                                                            */
/*          none used                                                       */
/*                                                                          */
/*      AUTOMATIC LOCALS:                                                   */
/*          unsigned char dud - dummy variable                              */
/*          unsigned short heidi - incrementer for the delay loops          */
```

```
/*                unsigned short loop - number of longer loops that are      */
/*                             performed                                      */
/*                                                                            */
/*      ARGUMENTS:                                                            */
/*          unsigned short time - total number of loops to be traversed       */
/*                                                                            */
/*      CONSTANTS:                                                            */
/*          none used                                                         */
/*                                                                            */
/******************************************************************************/ delay(time)
unsigned short time;
begin
    unsigned char dud;
    unsigned short heidi;
    unsigned short loop;
    loop = time >> 3;       /* One longer loop is performed for every seven */
    time -= loop;           /*    shorter loops                              */
    for (heidi = 0; heidi < time; ++heidi)   /* Perform short loops          */
        ;
    for (heidi = 0; heidi < loop; ++heidi)   /* Perform longer loops         */
        dud = 0;
end /******************************************************************************/
/*  DISERR.ERG  *                                                             */
/****************                                                             */
/*                                                                            */
/*  This routine will display the error code encountered during an           */
/*      EOG test. An 'E' appears in the left hand digit of the display        */
/*      followed by the code 1 if there is a noisy baseline, the code         */
/*      2 if the peak amplitude is off scale, and the code 3 if the           */
/*      amplitudes fluctuate too greatly. The right eye is selected           */
/*      by placing the display mode switch in the 'Irradiance' postion        */
/*      and the left eye is seleted by placing the display mode switch        */
/*      in the 'Flash Energy' position.                                       */
/*                                                                            */
/*      THIS ROUTINE CALLS:                                                   */
/*          display()                                                         */
/*                                                                            */
/*      GLOBALS:                                                              */
/*          hex                     r_err                                     */
/*          l_err                                                             */
/*                                                                            */
/*      AUTOMATIC LOCALS:                                                     */
/*          unsigned short data - used to send the code to the routine        */
/*                                display()                                   */
/*                                                                            */
/*      ARGUMENTS:                                                            */
/*          none used                                                         */
/*                                                                            */
/*      CONSTANTS:                                                            */
/*          IN1                     M_DISPLAY                                 */
/*                                                                            */
/******************************************************************************/ diserr()
    begin
    unsigned short data;
    hex = 1;
    data = 0xFE00;              /* Turn decimal points off and place an 'E' */
    if (in (IN1) & M_DISPLAY)   /* in the left hand digit of the display    */
        then data |= r_err;
        else data |= l_err;     /* Display requested error code             */
    display (data);
    end
```

```
/************************************************************************/
/*  DISPLY.ERG                                                          */
/*****************                                                      */
/*                                                                      */
/*  This routine will send the input argument to the digital display.   */
/*      It also controls the decimal points and the lights behind the   */
/*      messages, 'FLASH LENGTH', 'DOUBLE INTERVAL', and 'PRE-FLASH      */
/*      INTERVAL'.                                                      */
/*                                                                      */
/*      THIS ROUTINE CALLS:                                             */
/*          div()                                                       */
/*                                                                      */
/*      GLOBALS:                                                        */
/*          in_calib              d_one                                 */
/*          d_hund                d_ten                                 */
/*          high                  repeat                                */
/*          c_out2                hex                                   */
/*                                                                      */
/*      AUTOMATIC LOCALS:                                               */
/*          unsigned short decimal - code for which decimal points      */
/*                                   should be on                       */
/*                                                                      */
/*      ARGUMENTS:                                                      */
/*          unsigned short data - number to be displayed                */
/*                                                                      */
/*      CONSTANTS:                                                      */
/*          OUT_D1                OUT_D2                                */
/*          M_DSELECT                                                   */
/*                                                                      */
/************************************************************************/ display (data)
unsigned short data;
    begin
    unsigned short decimal;

if (in_calib)
        decimal = 0xF;      /* Turn decimal points off when in cal-     */
                            /*    ibration mode                         */
        else decimal = data >> 12;  /* Look-up tables contain the in-   */
                                    /*    formation for the decimal     */
                                    /*    points as the upper 4 bits    */
    data &= 0xFFF;
    if (hex)
        then
            begin                   /* Display data in hex format       */
            d_one = data & 0xF;
            d_ten = (data & 0xF0) >> 4;
            d_hund = (data & 0xF00) >> 8;
            hex = 0;
            end
        else d_one = div (div (data, 100, &d_hund), 10, &d_ten);
                /* Convert number to decimal */ if (high && repeat)   /* Put OFF onto the display to indicate that  */
            begin         /*    the light meter would be giving incorrect */
            out (OUT_D1, 0xFF);        /*   readings                    */
            out (OUT_D2, 0xF0);
            end
        else
            begin
            out (OUT_D1, (d_ten << 4) + d_one);   /* Format the numbers */
            d_hund += decimal << 4;               /*    for display     */
            out (OUT_D2, d_hund);
            end
```

```
        if (in_calib == 1)      /* Turn on the appropriate panel lamps if the */
            begin               /*   device is in trimpot calibration mode    */
            c_out2 &= ~M_DSELECT;
            c_out2 |= (~select & M_DSELECT);
            end
            else c_out2 |= M_DSELECT;

out (OUT2, c_out2);
    end

/***********************************************************************/
/*  DIVIDE.ERG  *                                                      */
/****************                                                      */
/*                                                                     */
/*  THE ROUTINE: divide(dividend,divisor,quotient)                     */
/*               ---------------------------------                     */
/*      This integer divide routine divides the dividend by the divisor */
/*      storing the result in the location pointed to by the quotient. */
/*      The remainder is returned by the routine. The dividend and the */
/*      divisor must be such that the expected result is between 0 and */
/*      15 inclusive.                                                  */
/*                                                                     */
/*      THIS ROUTINE CALLS: nothing                                    */
/*                                                                     */
/*      GLOBALS: none                                                  */
/*                                                                     */
/*      STATIC LOCALS: none                                            */
/*                                                                     */
/*      AUTOMATIC LOCALS: US temp                                      */
/*                        C  i                                         */
/*                                                                     */
/*      ARGUMENTS: US dividend, divisor                                */
/*                 PTR quotient                                        */
/*                                                                     */
/*      CONSTANTS: none                                                */
/*                                                                     */
/*                                                                     */
/***********************************************************************/ div(dividend,divisor,quotient)
unsigned short dividend,divisor,*quotient;
begin
  unsigned short temp;
  char i;

*quotient = 0;

for (i=3; i >= 0; --i)
        begin
        *quotient = *quotient << 1;
        temp = dividend >> i;

if (temp >= divisor) then
            begin
            ++(*quotient);
            dividend = (dividend & ~(~0<<i)) + ((temp - divisor) << i);
            end end return(dividend);                              /* the remainder */
    end /***********************************************************************/
/*  EOG.ERG   *                                                        */
/****************                                                      */
```

```
/*                                                                            */
/*    This routine controls the EOG test protocol. It sets the timers         */
/*       to call rst75() every minutes, initializes the globals to be         */
/*       used, calls rst75() for the first time, and then waits for           */
/*       the hardware to do the automatic callins of rst75(). Note            */
/*       that since rst75() will update the variable 'minutes', this          */
/*       routine will switch on the background light 15 minutes into          */
/*       the test, and after 30 minutes will plot the condensed EOG           */
/*       amplitudes. The background light and the timers are then             */
/*       turned off.                                                          */
/*                                                                            */
/*    THIS ROUTINE CALLS:                                                     */
/*        rst75()              conden()                                       */
/*        setbit()             resetbit()                                     */
/*        diserr()             display()                                      */
/*                                                                            */
/*    GLOBALS:                                                                */
/*        minutes              min_eos[2]                                     */
/*        max_eos[2]           r_err                                          */
/*        l_err                eos_fin                                        */
/*        c_out3                                                              */
/*                                                                            */
/*    AUTOMATIC LOCALS:                                                       */
/*        none used                                                           */
/*                                                                            */
/*    ARGUMENTS:                                                              */
/*        none used                                                           */
/*                                                                            */
/*    CONSTANTS:                                                              */
/*        COM1                 COM2                                           */
/*        STA_TI               STOP_TI                                        */
/*        R                    L                                              */
/*        IN1                  M_DEOG                                         */
/*        IN3                  OUT3                                           */
/*        M_DBACK              M_SBACK                                        */
/*                                                                            */
/****************************************************************************/ eos()
    begin
    /* Set both timers to 13,576 and start them. This will                    */
    /*    cause the hardware to call rst75() every minute.                    */
    out (0x84, 0x08);       /* Lower byte of timer count                      */
    out (0x85, 0x75);       /* Upper byte of timer count, and timer mode      */
                            /*    is set to a continuous square wave          */
    out (0xC4, 0x08);       /* Lower byte of timer count                      */
    out (0xC5, 0xF5);       /* Upper byte of timer count, and timer mode      */
                            /*    is set to continuous pulses                 */
    out (COM1, STA_TI);     /* Start timers   */
    out (COM2, STA_TI);
    minutes = 100;          /* Initialize globals   */
    min_eos[R] = min_eos[L] = 255;
    max_eos[R] = max_eos[L] = 0;
    r_err = l_err = 0;

rst75();

while (!(in(IN1) & M_DEOG) && !eos_fin)
        begin
        if (minutes >= 15)          /* Turn on background light               */
            setbit (M_SBACK, &c_out3, OUT3);
        if (minutes >= 30)          /* EOG procedure finished                 */
            then
                begin
                conden();
                eos_fin = 1;
                end
```

```
                else
                    if (r_err>0 || l_err>0)
                        then diserr();
                        else display (minutes);
            end
        if (in (IN3) & M_DBACK) resetbit (M_SBACK, &c_out3, OUT3);
        out (COM1, STOP_TI);    /* Stop RST 7.5 timers    */
        out (COM2, STOP_TI);
        end /***********************************************************************/
/*   FRACTN.ERG    *                                                    */
/*****************                                                      */
/*                                                                      */
/* This routine will output to the plotter the result of 'top'          */
/*      divided by 'bottom'.  Only two digits, the one to the right     */
/*      of the decimal point and the one to the left of the decimal     */
/*      point are printed.                                              */
/*                                                                      */
/*      THIS ROUTINE CALLS:                                             */
/*          serial()              output()                              */
/*          div()                                                       */
/*                                                                      */
/*      GLOBALS:                                                        */
/*          none used                                                   */
/*                                                                      */
/*      AUTOMATIC LOCALS:                                               */
/*          unsigned short digit - digit to be output                   */
/*          unsigned char byte - ASCII value of digit to be output      */
/*                                                                      */
/*      ARGUMENTS:                                                      */
/*          unsigned short top - dividend of the division               */
/*          unsigned short bottom - divisor of the division             */
/*                                                                      */
/*      CONSTANTS:                                                      */
/*          none used                                                   */
/*                                                                      */
/***********************************************************************/ fractn(top,bottom)
unsigned short top, bottom;
    begin
    unsigned short digit;
    unsigned char byte;
    unsigned short remain;
    serial("LB");        /* Mnemonic to initiate the printing of labels  */
    remain = div (top, bottom, &digit);
    byte = digit + 48;
    output (byte);       /* Output units digit                           */
    output ('.');
    div ((remain<<1)+(remain<<3), bottom, &digit);
    byte = digit + 48;
    output (byte);       /* Output digit immediately to the left of the  */
    output (' ');        /*    decimal point                             */
    end /***********************************************************************/
/*   INIT.ERG    *                                                      */
/*****************                                                      */
/*                                                                      */
/* This routine initializes all pertinent variables at the start of     */
/*      the program.                                                    */
/*                                                                      */
/*      THIS ROUTINE CALLS:                                             */
/*          adcpot()                                                    */
/*                                                                      */
```

```
/*      GLOBALS:                                                        */
/*          c_out1              c_out2                                  */
/*          t_tris              t_salvo                                 */
/*          t_double            select                                  */
/*          in_calib            flash                                   */
/*          error               crash                                   */
/*          repeat              single                                  */
/*          light_on            loop                                    */
/*          expected[]          c_out3                                  */
/*          eos_fin             r_err                                   */
/*          l_err               hex                                     */
/*                                                                      */
/*      AUTOMATIC LOCALS:                                               */
/*          none used                                                   */
/*                                                                      */
/*      ARGUMENTS:                                                      */
/*          none used                                                   */
/*                                                                      */
/*      CONSTANTS:                                                      */
/*          RECALL              DUD                                     */
/*          N_OFF               OUT1                                    */
/*          OUT2                COM1                                    */
/*          COM2                STOP_TI                                 */
/*          AD_TRIG             AD_GALVO                                */
/*          AD_DOUBLE           SER_STAT                                */
/*                                                                      */
/**********************************************************************/ init ()
    begin
    out (RECALL, DUD);    /* Put EEPROM table into shadow RAM         */
    c_out1 = c_out2 = c_out3 = N_OFF;   /* Turn off all output ports  */
    out (COM1, STOP_TI);
    out (COM2, STOP_TI);
    out (OUT1, c_out1);
    out (OUT2, c_out2);
    out (OUT3, c_out3);
    out (SER_STAT, 0xFA);   /* Set Mode for serial port, 7 bits, even  */
                            /*   parity, 2 stop bits                   */
    out (SER_STAT, 0x11);   /* Set Command Instruction for serial port */
    t_tris = adcpot (AD_TRIG, 5, 157);   /* Set pre-trigger interval   */
    t_salvo = adcpot (AD_GALVO, 3, 157); /* Set length of flash        */
    t_double = adcpot (AD_DOUBLE, 2, 1597); /* Set interval between    */
                                            /*   double flashes        */
    /* Initialize various flags   */
    select = 1;
    hex = eos_fin = r_err = l_err = 0;
    in_calib = flash = error = crash = repeat = single = light_on = loop = 0;

/* Initialize the expected flash values for all possible atten-    */
    /*   uation settings                                               */
    expected[0] = 231;
    expected[1] = 216;
    expected[2] = 205;
    expected[3] = 193;
    expected[4] = 184;
    expected[5] = 179;
    expected[6] = 172;
    expected[7] = 167;
    expected[8] = 160;
    expected[9] = 154;
    expected[10] = 149;
    expected[11] = 142;
    expected[12] = 140;
    expected[13] = 133;
    expected[14] = 132;
    expected[15] = 125;
```

```
    expected[16] = 121;
    expected[17] = 115;
    expected[18] = 110;
    expected[19] = 94;
    expected[20] = 82;
    expected[21] = 65;
    expected[22] = 49;
    expected[23] = 27;
    expected[24] = 24;
    expected[25] = 19;
    expected[26] = 16;
    expected[27] = 12;
    expected[28] = 10;
    expected[29] = 8;
    expected[30] = 6;
    expected[31] = 5;
    expected[32] = 4;
    expected[33] = 3;
    expected[34] = 2;
    expected[35] = 2;
    expected[36] = 2;
    expected[37] = 1;
    expected[38] = 1;
    expected[39] = 1;
    expected[40] = 1;
    end /****************************************************************************/
/*                                                                          */
/*    MOVE.ERG    *                                                         */
/*****************                                                          */
/*                                                                          */
/*  This routine will output the HPGL commands to move the plotter          */
/*     pen to the absolute location given by arguments x and y.             */
/*                                                                          */
/*     THIS ROUTINE CALLS:                                                  */
/*         div()              serial()                                      */
/*         output()                                                         */
/*                                                                          */
/*     GLOBALS:                                                             */
/*         none used                                                        */
/*                                                                          */
/*     AUTOMATIC LOCALS:                                                    */
/*         unsigned short d[4] - array into which the bcd digits            */
/*                               are placed                                 */
/*                                                                          */
/*         unsigned short step - incrementer for loops                      */
/*                                                                          */
/*         unsigned char byte - ASCII value of the digit to be output       */
/*                                                                          */
/*     ARGUMENTS:                                                           */
/*         unsigned short x,y - absolute location to which the plotter      */
/*                              pen should be moved                         */
/*                                                                          */
/*     CONSTANTS:                                                           */
/*         none used                                                        */
/*                                                                          */
/****************************************************************************/ move(x,y)
unsigned short x,y;
    begin
    unsigned short d[4];
    unsigned short step;
    unsigned char byte;
    serial("PA");                              /* Start of command sequence  */
    d[1] = div (div (x, 100, &d[3]), 10, &d[2]);   /* Convert the x          */
    for (step=3; step>0; step--)               /*    co-ordinate to BCD      */
```

```
            begin
            byte = d[step] + 48;              /* Convert the digit to ASCII  */
            output (byte);
            end
        output (',');
        d[1] = div (div (y, 100, &d[3]), 10, &d[2]);   /* Convert the y       */
        for (step=3; step>0; step--)          /*    co-ordinate to BCD       */
            begin
            byte = d[step] + 48;              /* Convert the digit to ASCII  */
            output (byte);
            end
        end /****************************************************************************/
/*   OPENGA.ERG  *                                                          */
/****************                                                           */
/*                                                                          */
/*   This routine will trigger the hardware integration circuitry,          */
/*       open the shutter for the appropriate time, close it, and           */
/*       disable the integrating circuitry.  The shutter may be held        */
/*       open for any reason by grounding the test pin on the side of       */
/*       the microprocessor board.                                          */
/*                                                                          */
/*       THIS ROUTINE CALLS:                                                */
/*           setbit()              resetbit()                               */
/*           delay()                                                        */
/*                                                                          */
/*       GLOBALS:                                                           */
/*           c_out1                salvo                                    */
/*           t_salvo                                                        */
/*                                                                          */
/*       AUTOMATIC LOCALS:                                                  */
/*           none used                                                      */
/*                                                                          */
/*       ARGUMENTS:                                                         */
/*           none used                                                      */
/*                                                                          */
/*       CONSTANTS:                                                         */
/*           M_GALVO               OUT1                                     */
/*           OUT_DAC               IN3                                      */
/*           M_H_GALVO             P_OFF                                    */
/*                                                                          */
/****************************************************************************/ open_salvo ()
    begin
    setbit (M_GALVO, &c_out1, OUT1);  /* Enable flash integration           */
    out (OUT_DAC, salvo);    /* Open shutter                                */ if (high)
        delay (240);     /* Shutter opening at high frequencies is pre-     */
                         /*    set to 15 milliseconds                       */
        else delay (t_salvo);   /* Otherwise, open time is determined       */
                                /*    by the global 't_salvo'               */
    while (!(in (IN3) & M_H_GALVO))  /* If test pin is grounded hold        */
        ;                            /*    open the shutter                 */ resetbit (M_GALVO, &c_out1, OUT1);  /* Disable flash integration        */
    out (OUT_DAC, P_OFF);   /* Close shutter                                */
    end /****************************************************************************/
/*   OUTPUT.ERG  *                                                          */
/****************                                                           */
/*                                                                          */
/*   This routine will send one byte to the RS232 interface via the         */
/*       8251A communications chip.  It will do so only if the 8251A        */
```

```
/*        buffer is empty and the device on the other end of the RS232     */
/*        link is ready to receive data.                                    */
/*                                                                          */
/*     THIS ROUTINE CALLS:                                                  */
/*         nothing                                                          */
/*                                                                          */
/*     GLOBALS:                                                             */
/*         none used                                                        */
/*                                                                          */
/*     AUTOMATIC LOCALS:                                                    */
/*         none used                                                        */
/*                                                                          */
/*     ARGUMENTS:                                                           */
/*         unsigned char byte - character to be sent to the commun-         */
/*                              ications chip                               */
/*                                                                          */
/*     CONSTANTS:                                                           */
/*         SER_STAT              M_EMPTY                                    */
/*         SER_DATA              M_READY                                    */
/*                                                                          */
/****************************************************************************/ output(byte)
unsigned char byte;
    begin
    while (((!(in(SER_STAT) & M_EMPTY)) || (!(in(SER_STAT) & M_READY))))
        ;                       /* Wait until 8251A is empty and the     */
                                /*    device on the other end of the RS232 */
                                /*    link is ready                       */
    out (SER_DATA, byte);
    end /****************************************************************************/
/*    PLOT.ERG    *                                                         */
/****************                                                           */
/*                                                                          */
/*   This routine will digitize the ouput from the a signal averager        */
/*       and output the right and left ERG waveforms to the HP 7470A        */
/*       graphics plotter via an RS232 link.  The B-wave latency and        */
/*       amplitude are obtained from the input signal and also              */
/*       annotated on the graph.  Note that the plotter is programed        */
/*       in HP Graphics Language mnemonics.                                 */
/*                                                                          */
/*     THIS ROUTINE CALLS:                                                  */
/*         serial()              move()                                     */
/*         adc()                 print()                                    */
/*                                                                          */
/*     GLOBALS:                                                             */
/*         t_trig                atten                                      */
/*         t_salvo               error                                      */
/*                                                                          */
/*     AUTOMATIC LOCALS:                                                    */
/*         unsigned short step - incrementer for loops                      */
/*         unsigned short x - current x-axis value                          */
/*         unsigned short y - current y-axis value                          */
/*         unsigned short x_min, y_min - co-ordinates of the A-wave         */
/*         unsigned short x_max, y_max - co-ordinates of the B-wave         */
/*                                                                          */
/*     ARGUMENTS:                                                           */
/*         none used                                                        */
/*                                                                          */
/*     CONSTANTS:                                                           */
/*         AD_X                  AD_Y                                       */
/*         AD_PEN                                                           */
/*                                                                          */
/****************************************************************************/
```

```
plot()
    begin
    unsigned short step, x, y, y_min, y_max, x_min, x_max;
    for (step=0; step<2; step++)
        begin
    y_min = 255;
    y_max = 0;
    serial("IN");
    serial("\33\56\100");              /* Set RS232 handshaking to pin 20  */
    serial("SP1;SC0,350,0,300");       /* Define co-ordinate area          */
    move (adc(AD_X), adc(AD_Y));
    serial("PD");
    while (adc (AD_PEN) < 100)  /* Pen down */
        begin                   /* Digitize and plot points, keeping a    */
        x = adc (AD_X);         /*   look-out for the A and B waves       */
        y = adc (AD_Y);
        if (y < y_min)
            begin
            y_min = y;
            x_min = x;
            end
        if (y > y_max)
            begin
            y_max = y;
            x_max = x;
            end
        move (x, y);
        delay (800);  /* 50 msec delay to prevent the plotter buffer */
        end           /*    from filling up with repeated points     */
    serial("PU;SP2;SM*");
    move (x_min, y_min);         /* Flag A-wave with an asterisk */
    move (x_max, y_max);         /* Flag B-wave with an asterisk */
    serial("PU;SM;");
    move (260, y);
    serial("DT ;LBLatency: ");          /* Print the latency and peak */
    print (x_max-(t_trig>>4)+1);        /*    B-wave amplitude        */
    serial("LBmsec ;CP;LBAmplitude: ");
    print ((y_max-y_min)<<1);
    serial("LBuV ");
    while ((adc(AD_PEN)>100) && (adc(AD_PEN)>100) && step==0)
        ;       /* Wait for plot of the ERG waveform for the next eye */
    end
serial("PA5,25PD0,25,0,0,20,0,20,5PU25,0");  /* Record scale */
serial("LB20msec PA0,30LB50uV ");
move ((t_trig>>4)+1, 36);
serial("PD;PR0,219PU;PR3,-5;LBTrigger ");  /* Mark when light was */
serial("CS0;SS;DT ;SC;");                  /*    triggered        */
serial("IP0,0,10300,7650");
serial("SI0.7,1.0");
serial("SP1;PA1570,7250");
serial("LBELECTRORETINOGRAM ");      /* Title graph */
serial("SP2");
serial("SI0.28,0.4");
serial("PA1200,6850");
serial("LBAttenuation: ");  /* Print out the stimulating parameters */
print (atten);
serial("LBdB ");
serial("PA5150,6850");
serial("LBChromatic LBFiltering: ");
switch ((c_out2 & 0x38) >> 3)
    begin
    case 7:
        serial("LBWhite ");
        break;
    case 6:
        serial("LBRed ");
        break;
```

```
                case 5:
                    serial("LBBlue ");
                    break;
                case 3:
                    serial("LBGreen ");
                    break;
                end
        serial("PA1200,6550");
        serial("LBFlash LBLength: ");
        print ((t_salvo>>4)+1);
        serial("LBmsec ");
        serial("PA5150,6550");
        serial("LBCalibration: ");
        if (error > 3)
            then serial("LBError ");
            else serial("LBO.K. ");
        serial("SP0;");
        end /**************************************************************************/
/*  PRINT.ERG   *                                                         */
/***************                                                          */
/*                                                                        */
/*  This routine will output three digits of the argument 'number'        */
/*      to the plotter.                                                   */
/*                                                                        */
/*      THIS ROUTINE CALLS:                                               */
/*          output()            div()                                     */
/*          serial()                                                      */
/*                                                                        */
/*      GLOBALS:                                                          */
/*          none used                                                     */
/*                                                                        */
/*      AUTOMATIC LOCALS:                                                 */
/*          unsigned short d[4] - array that holds the BCD values of      */
/*                                the argument                            */
/*          unsigned short step - incrementer for loops                   */
/*          unsigned char byte - ASCII digit to be sent to the plotter    */
/*                                                                        */
/*      ARGUMENTS:                                                        */
/*          unsigned short number - value to be printed                   */
/*                                                                        */
/*      CONSTANTS:                                                        */
/*          none used                                                     */
/*                                                                        */
/**************************************************************************/
print(number)
unsigned short number;
    begin
    unsigned short d[4];
    unsigned short step;
    unsigned char byte;
    serial("LB");           /* Output mnemonic to start printing labels  */
    d[1] = div (div (number, 100, &d[3]), 10, &d[2]);
    for (step=3; step>0; step--)
        begin                      /* Print 3 digits                     */
        byte = d[step] + 48;
        output (byte);
        end
    output (' ');
    end /**************************************************************************/
/*  RESETB.ERG   *                                                        */
/***************                                                          */
/*                                                                        */
/*  This routine resets the bits indicated by the argument 'bit_mask'     */
```

```
/*          to high, since all output ports use negative logic.  The          */
/*          status of the port is maintained in the appropriate global        */
/*          &c_out.                                                           */
/*                                                                            */
/*          THIS ROUTINE CALLS:                                               */
/*              nothing                                                       */
/*                                                                            */
/*          GLOBALS:                                                          */
/*              none used                                                     */
/*                                                                            */
/*          AUTOMATIC LOCALS:                                                 */
/*              none used                                                     */
/*                                                                            */
/*          ARGUMENTS:                                                        */
/*              unsigned short bit_mask - positive logic mask which           */
/*                                        indicates which bits are to be      */
/*                                        reset                               */
/*              unsigned short *c_out - pointer to the variable that keeps    */
/*                                        track of output port status         */
/*              unsigned short port - output port                             */
/*                                                                            */
/*          CONSTANTS:                                                        */
/*              none used                                                     */
/*                                                                            */
/******************************************************************************/ resetbit (bit_mask, c_out, port)
unsigned short bit_mask, *c_out, port;
    begin
    *c_out != bit_mask;     /* Change output status global                */
    out (port, *c_out);     /* Reset bits                                 */
    end /******************************************************************************/
/*    RST65.ERG   *                                                           */
/****************                                                             */
/*                                                                            */
/*  This routine is usually called by hardware to perform one flash           */
/*      sequence as determined by the value of several global                 */
/*      variables.  First a check is made if the flash light source is        */
/*      on, and if not, it is turned on and there is a delay of one           */
/*      second to allow the light source to warm up.  The routine             */
/*      smode is called to determine the current status of the control        */
/*      panel.  If the rate is 'low' or 'double', then a pre-trigger          */
/*      pulse is sent.  The shutter is opened by calling open_salvo().        */
/*      The energy of the flash is measured, and if it is not as              */
/*      expected, the 'OUT OF CALIBRATION' light is turned on.                */
/*      If the rate is 'double' then a second flash is performed.             */
/*                                                                            */
/*      THIS ROUTINE CALLS:                                                   */
/*          setbit()            resetbit()                                    */
/*          delay()             smode()                                       */
/*          adc()                                                             */
/*                                                                            */
/*      GLOBALS:                                                              */
/*          c_out1              light_on                                      */
/*          time                single                                        */
/*          low                 high                                          */
/*          doubl               t_trig                                        */
/*          b_flash             flash                                         */
/*          t_flash[]           f_expect                                      */
/*          expected[]          atten                                         */
/*          b_back              t_salvo                                       */
/*          range               l_range                                       */
/*          error               t_double                                      */
/*          crash                                                             */
/*                                                                            */
```

```
/*      AUTOMATIC LOCALS:                                                  */
/*          none used                                                      */
/*                                                                         */
/*      ARGUMENTS:                                                         */
/*          none used                                                      */
/*                                                                         */
/*      CONSTANTS:                                                         */
/*          M_RST65                 OUT1                                   */
/*          M_LIGHT                 M_TRIG                                 */
/*          AD_FLASH                AD_BACK                                */
/*          M_OUT_CAL                                                      */
/*                                                                         */
/*************************************************************************/ rst65()
    begin
    setbit (M_RST65, &c_out1, OUT1);  /* Hardware flag to indicate the    */
                                      /*   interupt has been entered      */
    if (!(light_on))
        begin              /* Flash light source is not on                 */
        setbit (M_LIGHT, &c_out1, OUT1);
        delay (16000);     /* Wait for 1 second to allow flash light       */
        light_on = 1;      /*   source to warm up                          */
        end time = 0;              /* Reset time since last flash  */ if (single == 1)       /* Indicate that single flash is being processed */
        single = 2;

low = high = doubl = 0;
    smode ();

switch (mode)          /* Set variables according to the readings of   */
        begin              /*   the RATE switch on the control panel       */
        case 2:
            high = 1;
            break;
        case 1:
            doubl = 1;
            break;
        default:
            low = 1;
            break;
        end if (doubl || low)      /* Output pre-trigger pulse */
        begin
        setbit (M_TRIG, &c_out1, OUT1);
        delay (t_trig);
        resetbit (M_TRIG, &c_out1, OUT1);
        end open_galvo ();                    /* Open galvanometer shutter */ if (!(high && repeat))
        begin
        b_flash = adc (AD_FLASH);
        flash = t_flash[b_flash];     /* Find calibrated value of flash    */
            /* Find expected value of flash, that is corrected             */
            /*   according to background irradiance and length of flash    */
        f_expect = (expected[atten] - b_back) * (t_galvo >> 4) / 20;
            /* Find allowable range of error                               */
        range = ((expected[atten] + b_back) >> 3 ) + 3;
            /* Make sure lower range is not negative    */
        l_range = f_expect - range;
```

```
            if (l_range < 0) l_range = 0;
            if ((b_flash <= f_expect + range) && (b_flash >= l_range))
                error = 0;            /* No error          */
                else error += 1;      /* Error detected    */
            end
        if ((error > 3) && (!high))
            setbit (M_OUT_CAL, &c_out1, OUT1);  /* If three errors in a row    */
                                /*    then turn on OUT OF CALIBRATION light */
            else resetbit (M_OUT_CAL, &c_out1, OUT1);

if (doubl)      /* If rate is double then perform one more flash    */
            begin
            delay (t_double);
            open_salvo ();
            end if (crash)                      /* Restore ADC buffer to contain a   */
            adc (AD_BACK);              /*    background reading             */ resetbit (M_RST65, &c_out1, OUT1);   /* Reset hardware flag           */
end

/************************************************************************/
/*      RST75.ERG  *                                                     */
/*****************                                                       */
/*                                                                       */
/*  This routine will turn on the oscillating LEDs used for the EOG      */
/*      test and measure the right and left amplitudes obtained for     */
/*      5 cycles. An attempt is made to find 3 amplitudes which are     */
/*      close together, the average of which is stored as the amplitude */
/*      for that minute. If the attempt fails for the right eye then    */
/*      r_err is set to 3, and if the attempt fails for the left eye    */
/*      then l_err is set to 3.                                          */
/*                                                                       */
/*      THIS ROUTINE CALLS:                                              */
/*          setbit()             resetbit()                              */
/*          amplit()             diserr()                                */
/*          display()                                                    */
/*                                                                       */
/*      GLOBALS:                                                         */
/*          minutes              c_out1                                  */
/*          eos_a[2][31]         r_err                                   */
/*          l_err                                                        */
/*                                                                       */
/*      AUTOMATIC LOCALS:                                                */
/*          unsigned short eye - eye that is being processed             */
/*          unsigned short step, bill - incrementers for loops           */
/*          unsigned short count - number of valid amplitudes found      */
/*          unsigned short finished - positive logic flag to indicate    */
/*                                    if 3 valid amplitudes have been    */
/*                                    found                              */
/*          unsigned short total - total used to find averages           */
/*          unsigned short deviation - deviation from other amplitudes   */
/*                                                                       */
/*      ARGUMENTS:                                                       */
/*          none used                                                    */
/*                                                                       */
/*      CONSTANTS:                                                       */
/*          M_SEOG               M_DEOG                                  */
/*          M_CEOG               OUT1                                    */
/*          IN1                  IN3                                     */
/*                                                                       */
/************************************************************************/ rst75()
    begin
```

```c
unsigned short eye, step, count, bill, finished, total, deviation;
unsigned short amp[2][6];
minutes += 1;
if (minutes>100) minutes = 0;      /* First time rst75() is called     */
setbit(M_SEOG, &c_out1, OUT1);     /* Turn on EOG lights               */
for (step=1; step<6; step++)
    if (!(in(IN1) & M_DEOG))
        begin
        while (!(in(IN3) & M_CEOG))
            ;            /* Wait for positive EOG sync              */
        amplit (&[0][step], &[1][step]);
        if (r_err>0 || l_err>0)
            then diserr();
            else if (in (IN1) & M_DISPLAY)
                    then display (amp[0][step]); /* Display ampli-   */
                    else display (amp[1][step]); /*   tude if no     */
        while (in(IN3) & M_CEOG)                 /*   error          */
            ;            /* Wait for EOG sync to go down again       */
        end
resetbit (M_SEOG, &c_out1, OUT1);   /* Turn off EOG lights             */
if (!(in(IN1) & M_DEOG))
    begin
    for (eye=0; eye<2; eye++)        /* For each eye                   */
        begin
        finished = 0;
        step = 5;
        while (!finished)
            begin         /* Starting with the back values, find       */
            total = amp[eye][step]; /* at least 3 amplitudes that      */
            count = 1;              /* are close together              */
            for (bill=step-1; bill>0; bill--)
                begin
                if (amp[eye][step] > amp[eye][bill])
                    then deviation = amp[eye][step] - amp[eye][bill];
                    else deviation = amp[eye][bill] - amp[eye][step];
                if (deviation < 50)
                    begin
                    count += 1;
                    total += amp[eye][bill];
                    end
                end
            if (count >= 3)
                then          /* At least 3 amplitudes found           */
                    begin
                    eos_a[eye][minutes] = total/count;  /* Find       */
                    if (eos_a[eye][minutes] != 0)        /*   average */
                        if (minutes <= 15)
                            then    /* Find the min. dark amplitude */
                                begin
                                if (eos_a[eye][minutes] < min_eos[eye])
                                    min_eos[eye] = eos_a[eye][minutes];
                                end
                                    /* Find the max. light amplitude */
                            else if (eos_a[eye][minutes] > max_eos[eye])
                                max_eos[eye] = eos_a[eye][minutes];
                    finished = 1;
                    end
                else if (step = 3)
                        then                /* Amplitudes not close   */
                            begin           /*   enough               */
                            if (eye==0)
                                then r_err = 3;
                                else l_err = 3;
                            finished = 1;
                            end
                        else
```

```
                              begin
                              step--;
                              if (eye==0)
                                  then r_err = 0;
                                  else l_err = 0;
                              end
                      end
                 end
             end
        end
```

```
/***********************************************************************/
/*   SERIAL.ERG  *                                                     */
/****************                                                      */
/*                                                                     */
/*  This routine will send the string '*message' to the plotter via    */
/*      the RS232 link.                                                */
/*                                                                     */
/*      THIS ROUTINE CALLS:                                            */
/*          output()                                                   */
/*                                                                     */
/*      GLOBALS:                                                       */
/*          none used                                                  */
/*                                                                     */
/*      AUTOMATIC LOCALS:                                              */
/*          unsigned short step - incrementer for loops                */
/*                                                                     */
/*      ARGUMENTS:                                                     */
/*          unsigned char *message - pointer to the string to be       */
/*                                   sent to the plotter               */
/*                                                                     */
/*      CONSTANTS:                                                     */
/*          none used                                                  */
/*                                                                     */
/***********************************************************************/ serial(message)
unsigned char *message;
    begin
    unsigned short step;
    step = 0;
    while (message[step] != '\0')      /* Send the string to the routine  */
        begin                          /*    output() one character at a  */
        output (message[step]);        /*    time                         */
        step++;
        end
    end
```

```
/***********************************************************************/
/*   SETBIT.ERG  *                                                     */
/****************                                                      */
/*                                                                     */
/*  This routine sets the bits indicated by the argument 'bit_mask'    */
/*      to low, since all the output ports use negative logic. The     */
/*      status of the port is maintained in the appropriate global     */
/*      &c_out.                                                        */
/*                                                                     */
/*      THIS ROUTINE CALLS:                                            */
/*          nothing                                                    */
/*                                                                     */
/*      GLOBALS:                                                       */
/*          none used                                                  */
/*                                                                     */
/*      AUTOMATIC LOCALS:                                              */
/*          none used                                                  */
/*                                                                     */
/*      ARGUMENTS:                                                     */
```

```
/*              unsigned short bit_mask - positive logic mask which       */
/*                                  indicates which bits are to be        */
/*                                  set                                   */
/*              unsigned short *c_out - pointer to the variable that keeps*/
/*                                  track of output port status           */
/*              unsigned short port - output port                         */
/*                                                                        */
/*      CONSTANTS:                                                        */
/*          none used                                                     */
/*                                                                        */
/**************************************************************************/ setbit (bit_mask, c_out, port)
unsigned short bit_mask, *c_out, port;
    begin
    *c_out &= ~bit_mask;        /* Change output status global            */
    out (port, *c_out);         /* Set bits                               */
    end /**************************************************************************/
/*  SMODE.ERG   *                                                         */
/*****************                                                        */
/*                                                                        */
/*  This routine reads most of the control panel switches and also        */
/*      takes care of a few housekeeping items. It reads the thumb-       */
/*      wheel attenuation switch and sets the global 'salvo' to the       */
/*      desire shutter opening. The 'single' switch is read to see        */
/*      if a single flash sequence is desired. The background switch      */
/*      is read and the background light set accordingly. The rate        */
/*      switch is read to determine the mode of operation. The repeat     */
/*      switch is checked and also the chromatic filter switch is read    */
/*      and the appropriate filters are set. This routine also turns      */
/*      off the flash light source if about 5 minutes has passed.         */
/*                                                                        */
/*      THIS ROUTINE CALLS:                                               */
/*          resetbit()              setbit()                              */
/*                                                                        */
/*      GLOBALS:                                                          */
/*          time                    light_on                              */
/*          c_out1                  thumb                                 */
/*          bcd[]                   atten                                 */
/*          salvo                   t_cal[]                               */
/*          single                  mode                                  */
/*          repeat                  c_out2                                */
/*          c_out3                                                        */
/*                                                                        */
/*      AUTOMATIC LOCALS:                                                 */
/*          unsigned short sherry - incrementing variable for loops       */
/*                                                                        */
/*      ARGUMENTS:                                                        */
/*          none used                                                     */
/*                                                                        */
/*      CONSTANTS:                                                        */
/*          M_LIGHT                 OUT1                                  */
/*          IN2                     IN3                                   */
/*          M_SINGLE                M_DBACK                               */
/*          M_SBACK                 IN1                                   */
/*          M_MODE                  M_INTER                               */
/*          M_REPEAT                F_OFF                                 */
/*          F_HIGH                  F_LOW                                 */
/*          OUT1                    OUT2                                  */
/*          M_CHROM                 OUT3                                  */
/*                                                                        */
/**************************************************************************/
```

```
smode ()
    begin
    unsigned short sherry;
    time += 1;
    if (time > 32000 && light_on)
        begin                              /* Time to switch off flash light */
        resetbit (M_LIGHT, &c_out1, OUT1); /*    source                      */
        light_on = 0;
        end thumb = ~(in (IN2)) & 0xFF;    /* Read thumbwheel attenuation switch */
    bcd[1] = thumb & 0x0F;
    bcd[2] = thumb >> 4;
    atten = 0;

for (sherry = 2; sherry > 0; --sherry) /* Convert the BCD to binary */
        atten = (atten << 1) + (atten << 3) + bcd[sherry];

atten &= 0xFF;
    if (atten > 40)
        then
            begin
            atten = 40;    /* Do not allow the attenuation to be greater */
            salvo = 0;     /*    than 40 dB                              */
            end
        else salvo = t_cal[atten]; /* Get calibrated shutter opening    */ if (!(in(IN3) & M_SINGLE))   /* Check if front panel single switch  */
            begin                /*    is held                          */
            if (single != 2)
                single = 1;
            end
        else single = 0;

if (in(IN3) & M_DBACK)     /* Read background light switch and set */
        resetbit (M_SBACK, &c_out3, OUT3);  /*  or reset the light     */
        else setbit (M_SBACK, &c_out3, OUT3);  /*  accordingly         */ mode = (in(IN1) & M_MODE) >> 2;  /* Read the rate switch on contrl */
    c_out1 &= ~M_INTER;              /*    panel                       */ if (in (IN1) & M_REPEAT)         /* Repeat switch is off  */
            begin
            c_out1 |= F_OFF;
            repeat = 0;
            end
        else
            begin
            repeat = 1;

if (mode == 2)              /* Find desired interupting   */
                c_out1 |= F_HIGH;       /*    frequency               */
                else c_out1 |= F_LOW;
            end out (OUT1, c_out1);              /* Set hardware interrupt sequence */
    c_out2 &= ~0x38;                 /* Set chromatic fliters           */
    c_out2 |= (in (IN1) & M_CHROM) >> 1;
    out (OUT2, c_out2);

end

/***************************************************************************/
/*    TRAP.ERG    *                                                        */
/****************                                                          */
/*                                                                         */
/* This interupt is not used by the ERG program.                           */
```

```
/*                                                                        */
/**************************************************************************/ trap ()
    begin
    end

/**************************************************************************/
/*   HDRERG.8   *                                                          */
/**************                                                            */
/*                                                                        */
/*   This routine is used by the Whitesmith 'C' compiler to place all     */
/*      the compiled 'C' programs into their appropriate machine          */
/*      language locations for the Intel 8085 microprocessor. It sets     */
/*      up the stack pointer, and saves and restores the status of        */
/*      the processor during interupts. This routine also places the      */
/*      two look-up tables for calibrating the background irradiance      */
/*      and flash energy directly into EPROM memory.                      */
/*                                                                        */
/**************************************************************************/ stack := 0x3300
sim:             0x3e,0x19,0x30
                 jmp startup
. := .[0x1e]
trp:             call preserve
                 call _trap
                 ret
. := .[0x9]
r6.5:            call preserve
                 call _rst65
                 ret
. := .[0x1]
r7.5:            call preserve
                 call _rst75
                 ret
. := .[0x1]
                 /* Look-up table to translate background ADC readings */
                 /*   to microwatts/cm.cm starts at 44 (hex)           */
bdata:           "\0\160\31\160\61\160\112\160\143\160"
                 "\14\260\17\260\22\260\24\260\27\260"
                 "\32\260\34\260\37\260\42\260\44\260"
                 "\47\260\52\260\55\260\60\260\63\260"
                 "\65\260\70\260\73\260\76\260\101\260"
                 "\104\260\110\260\113\260\116\260\121\260"
                 "\124\260\127\260\133\260\136\260\141\260"
                 "\12\320\12\320\13\320\13\320\13\320"
                 "\14\320\14\320\15\320\15\320\15\320"
                 "\16\320\16\320\16\320\17\320\17\320"
                 "\20\320\20\320\20\320\21\320\21\320"
                 "\22\320\22\320\22\320\23\320\23\320"
                 "\24\320\24\320\25\320\25\320\26\320"
                 "\26\320\27\320\27\320\30\320\30\320"
                 "\31\320\31\320\32\320\32\320\33\320"
                 "\33\320\34\320\34\320\35\320\35\320"
                 "\36\320\36\320\37\320\40\320\40\320"
                 "\41\320\41\320\42\320\43\320\43\320"
                 "\44\320\45\320\45\320\46\320\47\320"
                 "\47\320\50\320\51\320\52\320\52\320"
                 "\53\320\54\320\55\320\55\320\56\320"
                 "\57\320\60\320\61\320\62\320\62\320"
                 "\63\320\64\320\65\320\66\320\67\320"
                 "\70\320\71\320\72\320\73\320\74\320"
                 "\75\320\76\320\77\320\100\320\102\320"
                 "\103\320\104\320\105\320\106\320\110\320"
                 "\111\320\112\320\113\320\115\320\116\320"
                 "\120\320\121\320\123\320\124\320\126\320"
```

```
"\127\320\36\260\101\260\12\320\16\320"
"\22\320\26\320\32\320\36\320\43\320"
"\50\320\55\320\62\320\67\320\74\320"
"\102\320\110\320\116\320\124\320\133\320"
"\141\320\12\340\13\340\14\340\15\340"
"\16\340\16\340\17\340\20\340\21\340"
"\22\340\23\340\24\340\25\340\27\340"
"\30\340\31\340\32\340\34\340\35\340"
"\37\340\40\340\42\340\44\340\46\340"
"\47\340\51\340\54\340\56\340\60\340"
"\63\340\65\340\70\340\73\340\76\340"
"\101\340\105\340\110\340\114\340\120\340"
"\125\340\132\340\137\340\144\340\152\340"
"\161\340\170\340\200\340\210\340\221\340"
"\233\340\246\340\263\340\301\340\320\340"
"\342\340\366\340\15\341\50\341\110\341"
"\156\341\234\341\325\341\36\342\176\342"
"\2\343\102\343\366\344\61\347\300\354"
"\303\22\76\221\16\62\143\260\152\265"
"\153\266\307\114\347\33\331\161\234\170"
"\307\110\272\361\213\175\42\363\142\127"
"\327\255\45\371\116\73\341\165\25\252"
"\344\330\25\3\116\51\23\114\326\153"
"\364\210"
```

. := .[0x1]

/* Look-up table to translate flash ADC readings */
/* to microJoules/cm.cm starts at 245 (hex)     */ fdata:
```
"\0\160\1\160\1\160\2\160\2\160"
"\3\160\3\160\4\160\4\160\5\160"
"\5\160\6\160\6\160\7\160\10\160"
"\10\160\11\160\11\160\11\160\12\160"
"\12\160\13\160\13\160\14\160\14\160"
"\15\160\15\160\16\160\16\160\17\160"
"\17\160\20\160\20\160\20\160\21\160"
"\21\160\22\160\22\160\23\160\23\160"
"\23\160\24\160\24\160\25\160\25\160"
"\25\160\26\160\26\160\27\160\27\160"
"\27\160\30\160\30\160\31\160\31\160"
"\31\160\32\160\32\160\32\160\33\160"
"\33\160\33\160\34\160\34\160\35\160"
"\35\160\35\160\36\160\36\160\36\160"
"\37\160\37\160\37\160\40\160\40\160"
"\40\160\41\160\41\160\41\160\42\160"
"\42\160\42\160\43\160\43\160\43\160"
"\43\160\44\160\44\160\44\160\45\160"
"\45\160\45\160\46\160\46\160\46\160"
"\46\160\47\160\47\160\47\160\50\160"
"\50\160\50\160\50\160\51\160\51\160"
"\51\160\51\160\52\160\52\160\52\160"
"\53\160\53\160\53\160\53\160\54\160"
"\54\160\54\160\54\160\55\160\55\160"
"\55\160\26\160\41\160\55\160\70\160"
"\103\160\117\160\133\160\12\260\13\260"
"\15\260\16\260\17\260\20\260\22\260"
"\23\260\24\260\25\260\27\260\30\260"
"\31\260\33\260\34\260\35\260\37\260"
"\40\260\41\260\43\260\44\260\45\260"
"\47\260\50\260\52\260\53\260\55\260"
"\56\260\57\260\61\260\62\260\64\260"
"\65\260\67\260\70\260\72\260\73\260"
"\75\260\77\260\100\260\102\260\103\260"
"\105\260\106\260\110\260\112\260\113\260"
"\115\260\116\260\120\260\122\260\123\260"
"\125\260\127\260\130\260\132\260\134\260"
"\135\260\137\260\141\260\143\260\12\320"
"\12\320\12\320\13\320\13\320\13\320"
"\13\320\13\320\13\320\14\320\14\320"
"\14\320\14\320\14\320\15\320\15\320"
"\15\320\15\320\15\320\15\320\16\320"
```

```
"\16\320\16\320\16\320\16\320\17\320"
"\17\320\17\320\17\320\17\320\17\320"
"\20\320\20\320\20\320\20\320\20\320"
"\21\320\21\320\21\320\21\320\21\320"
"\22\320\22\320\22\320\22\320\22\320"
"\23\320\23\320\23\320\23\320\23\320"
"\24\320\24\320\24\320\24\320\24\320"
"\25\320\25\320\25\320\25\320\25\320"
"\26\320\26\320\26\320\26\320\27\320"
"\27\320"

. := .[0x1]
startup:        sp = &stack
                ei
                call _main
                hlt
/*
/*
/*              Procedures to save & restore the volatile C environment
/*              during interrupt service.these routines  are reentrant.
/*
/*
preserve:       hl <> *sp           /* save regs & move ret addr */
                hl => sp
                de => sp
                bc => sp
```

We claim:

1. A visual stimulator, comprising:
   light directing means for directing light from a light source into a subject's eyes;
   attenuator means for selectably attenuating said light source;
   photo-detector means for producing a first output signal representative of the radiant energy directed onto the subject's eyes; and
   signal processing means for receiving and processing said first output signal to derive therefrom further output signals representative of the radiometric or photometric characteristics of said radiant energy;
   said attenuator means including:
   (a) a first shutter leaf affixed to a first galvanometer shaft; and,
   (b) a second shutter leaf affixed to a second galvanometer shaft;
   wherein said shutter leaves are positioned for pivotal movement with said galvanometer shafts to attenuate light from said light source passing between said shutter leaves.

2. A visual stimulator as defined in claim 1, further comprising attenuation control means for selectably varying current signals applied to said galvanometers to selectably pivot said shutter leaves, thereby selectably varying said attenuation.

3. A visual stimulator as defined in claim 2, further comprising:
   (a) a first notch in said first shutter leaf; and,
   (b) a second notch in said second shutter leaf; wherein said shutter leaves are positioned to define a light attenuating aperture between said notches.

4. A visual stimulator as defined in claim 3, wherein said shutter leaves and notches are positioned such that pivotal movement of said shutter leaves varies the area of said aperture, thereby varying said attenuation.

5. A visual stimulator as defined in claim 4, wherein said notches are shaped such that the area of said aperture varies in proportion to the exponential of the distance between said leaves.

6. A visual stimulator as defined in claim 2, wherein said attentuation control means enables repeated application of selectably variable current signals to said galvanometers, thereby interrupting and selectably attenuating said light source.

7. A visual stimulator, comprising:
   light directing means for directing light from a light source into a subject's eyes;
   attenuator means for selectably attenuating said light source;
   photo-detector means for producing a first output signal representative of the radiant energy directed onto the subject's eyes; and
   signal processing means for receiving and processing said first output signal to derive therefrom further output signals representative of the radiometric or photometric characteristics of said radiant energy, including a second output signal representative of the light flux at said photo-detector means, and wherein said signal processing means compares said second output signal with a calibration signal representative of the light flux expected from said light source and produce an alarm signal if said signals differ by more than a pre-selected amount.

8. A visual stimulator as defined in claim 7, wherein said signal processing means calibrates said attenuator means by:
   (a) selecting an initial attenuation setting of said attenuator means;
   (b) activating said light source;
   (c) comparing said second output signal with said calibration signal;
   (d) if said signals differ by no more than a preselected amount, storing said attenuation setting, selecting the next sequential attenuation setting of said attenuator means and returning to step (b); and,
   (e) if said signals differ by more than a preselected amount, selecting the next sequential attenuation setting of said attenuator means and returning to step (b).

* * * * *